United States Patent
Gangjee

(10) Patent No.: US 11,091,500 B2
(45) Date of Patent: *Aug. 17, 2021

(54) TRICYCLIC COMPOUNDS HAVING ANTIMITOTIC AND/OR ANTITUMOR ACTIVITY AND METHODS OF USE THEREOF

(71) Applicant: Duquesne University of the Holy Spirit, Pittsburgh, PA (US)

(72) Inventor: Aleem Gangjee, Allison Park, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/530,591

(22) Filed: Aug. 2, 2019

(65) Prior Publication Data

US 2019/0359630 A1 Nov. 28, 2019

Related U.S. Application Data

(60) Division of application No. 15/795,801, filed on Oct. 27, 2017, now Pat. No. 10,414,777, which is a division of application No. 15/283,705, filed on Oct. 3, 2016, now Pat. No. 9,802,955, which is a division of application No. 14/719,824, filed on May 22, 2015, now Pat. No. 9,458,167, which is a division of application No. 13/151,536, filed on Jun. 2, 2011, now Pat. No. 9,056,869, which is a continuation of application No. 12/170,633, filed on Jul. 10, 2008, now Pat. No. 7,982,035, which is a continuation-in-part of application No. 11/845,143, filed on Aug. 27, 2007, now Pat. No. 7,960,400.

(51) Int. Cl.
| | |
|---|---|
| *C07D 495/04* | (2006.01) |
| *C07D 487/04* | (2006.01) |
| *C07D 491/048* | (2006.01) |
| *A61K 31/519* | (2006.01) |

(52) U.S. Cl.
CPC .......... *C07D 495/04* (2013.01); *A61K 31/519* (2013.01); *C07D 487/04* (2013.01); *C07D 491/048* (2013.01)

(58) Field of Classification Search
CPC ..... A61K 31/519; A61P 35/00; C07D 487/04; C07D 491/048; C07D 495/04
See application file for complete search history.

(56) References Cited

U.S. PATENT DOCUMENTS

| | | | |
|---|---|---|---|
| 4,769,378 A | 9/1988 | Hirsch et al. | |
| 5,032,594 A | 7/1991 | Takehiko et al. | |
| 5,679,683 A * | 10/1997 | Bridges | C07D 239/70 514/53 |
| 6,596,726 B1 | 7/2003 | Bridges et al. | |
| 7,326,712 B2 | 2/2008 | Hurley et al. | |
| 7,468,373 B2 | 12/2008 | Heintzelman et al. | |
| 7,947,682 B2 | 5/2011 | Neamati | |
| 7,960,400 B2 | 6/2011 | Gangjee | |
| 7,982,035 B2 | 7/2011 | Gangjee | |
| 8,309,564 B2 * | 11/2012 | Gangjee | C07D 495/04 514/267 |
| 8,871,776 B2 | 10/2014 | Gangjee | |
| 9,056,869 B2 | 6/2015 | Gangjee | |
| 9,458,167 B2 | 10/2016 | Gangjee | |
| 2004/0127510 A1 | 7/2004 | Heintzelman et al. | |
| 2005/0227992 A1 | 10/2005 | Hurley et al. | |
| 2008/0045529 A1 * | 2/2008 | Eggenweiler | A61P 13/12 514/234.2 |
| 2015/0141445 A1 | 5/2015 | Gangjee | |

FOREIGN PATENT DOCUMENTS

| | | |
|---|---|---|
| GB | 1262864 | 2/1972 |
| IN | 157280 | 2/1986 |
| WO | 95/19970 | 7/1995 |
| WO | 98/29397 | 7/1998 |
| WO | 02/088138 | 11/2002 |
| WO | 03/037898 | 5/2003 |
| WO | 2005033288 | 4/2005 |
| WO | 2005037825 | 4/2005 |
| WO | 2006044524 | 4/2006 |
| WO | 2006093518 | 9/2006 |
| WO | 2006136402 | 12/2006 |

OTHER PUBLICATIONS

Rosowsky, A., et al., One-Step Synthesis of Novel 2,4-Diaminopyrimidine Antifolates from Bridged Alicyclic Ketones and Cyanoguanidine, 1999, J. Heterocyclic Chem. pp. 723-728, vol. 36.
International Search Report (PCT/ISA/210) and Written Opinion of the International Searching Authority (PCT/ISA/237) for PCT/US2009/049913 dated Aug. 24, 2009.
Showalter et al., "Tyrosine Kinase Inhibitors. 16. 6,4,6-Tricyclic Benzothieno[3,2-d]pyrimidines and Pyrimido[5,4-b]- and [4,5-b]bindoles as Potent Inhibitors of the Epidermal Growth Factor Receptor Tyrosine Kinase", Journal of Medicinal Chemistry 42(26), 5464-5474 (1999).
Konno, et al., "Synthesis of thieno[2,3-d]pyrimidine Derivatives and Their Antifungal Activities", Yakugaku Zasshi 109(7), 464-73 (1989).
Yamaguchi, et al., "3,4-Dihydrothienopyrimidines. II. Synthesis and Sodium Borohydride Reduction of 2-substituted 4-chloro-and 4-unsubstituted-thieno[2,3-d]pyrimidines", Chemical & Pharmaceutical bulletin 30(1), 326-32 (1982).

(Continued)

*Primary Examiner* — Erich A Leeser
(74) *Attorney, Agent, or Firm* — Buchanan Ingersoll & Rooney PC; Craig G. Cochenour, Esq.

(57) ABSTRACT

The present invention provides tricyclic compounds, and pharmaceutically acceptable salts thereof, having antimitotic activity, anti-multidrug resistance activity, for example P-glycoprotein inhibition, and antitumor activity, and which inhibit paclitaxel sensitive and resistant tumor cells. Also provided are methods of utilizing these compounds for treating tumor cells and inhibiting mitosis of cancerous cells.

1 Claim, 13 Drawing Sheets

(56) References Cited

OTHER PUBLICATIONS

Wolff, Manfred, E., Burger's Medicinal Chemistry and Drug Discovery, Fifth Ed., vol. 1; Principles and Practice, John Wiley & Sons, 1995, 975.
Banker, Gilbert S., et al., "Modern Pharmaceutics", Marcel Dekker, New York 1996, p. 596.
International Search Report for PCT/US08/73824 dated Nov. 7, 2008 (PCT/ISA/220 and PCT/ISA/210).
Written Opinion of the International Searching Authority for PCT/US08/73824 dated Nov. 7, 2008 (PCT/ISA/237).
Ngamga, et al., "Millaurine and Aceytlmillaurine Alkaloids from Millettia laurentii", J. of Nat. Prod., vol. 56, No. 12, pp. 2126-2132 (1993).
Rosowsky, et al., Synthesis of 2,4-diamino-9H-indeno[2,1-d]pyrimidines, 6(5), 613-22, J. of Het. Chem (1969).
Supplementary European Search for EP Application No. 08828802.2 dated Mar. 18, 2011.
Nelson et al., "Dicyclic and Tricyclic Diaminopyrimidine Derivatives as Potent Inhibitors of Cryptosporidium parvum Dihydrofolate Reductase", Antimicrobial Agents and Chemotherapy, Dec. 1, 2001 American Society for Microbiology, Washington, DC, US—ISSN 0066-4804, vol. 45, No. 12, pp. 3293-3303.
Nelson et al., "Erratum: Dicyclic and Tricyclic Diaminopyrimidine Derivatives as Potent Inhibitors of Cryptosporidium parvum Dihydrofolate Reductase: Structure-Activity and Structure-Selectivity Correlations", Mar. 2002, Antimicrobial Agents and Chemotherapy, vol. 46, No. 3, p. 940.
Elslager et al., "Folate antagonists. 6. Synthesis and antimalarial effects of fused 2,4-diaminothieno[2,3-d] pyrimidines (1-3)", Journal of Heterocyclic Chemistry, Aug. 1972 Wiley-Blackwell Publishing, Inc., US—ISSN 0022-152X, vol. 9, pp. 775-782.
Rosowsky et al., "Synthesis of 2,4-diamino-9H-indeno[2,1-d]pyrimidines", Journal of Heterocyclic Chemistry, Oct. 1969 Wiley-Blackwell Publishing, Inc. US—ISSN 0022-152X, vol. 6, pp. 613-622.
Higashino, et al., Triazolo[4,5-d]pyrimidines. VII. The Photochemical Transformation of 3-phenyl-3H-1,2,3-triazolo[4,5-d]pyrimidines into 9H-pyrimido[4,5-b]indoles, Heterocycles, vol. 15, No. 1, (1981).
Dotzauer et al., "2-4-Diamino-9H-pyrimido[4,5-b]indol-5-ols: Synthesis, invitro cytotoxic activity, and QSAR investigations", Bioorganic & Medical Chemistry, vol. 14 (21), pp. 7282-7292, (2006).
EP Communication pursuant to Article 94(3) EPC for EP 097951073 dated Jan. 30, 2019.
EP Communication pursuant to Article 94(3) EPC for EP 14172196.9 dated Jan. 31, 2019.
Rosowsky, et al., One-Step Synthesis of Novel 2,4-Diaminopyrimidine Antifolates from Bridged Alicyclic Ketones and Cyanoguanidine, 1999, J. Het Chem., 36-723-728.
Communication Pursuant to Article 94(3) EPC for EP Application No. 14172196.9-1109 dated Nov. 6, 2019.

\* cited by examiner

Figure 1. Microtubule Depolymerization Immunofluorescence Assay in A-10 Cells

Control

Figure 2. Microtubule Depolymerization
Immunofluorescence Assay in A-10 Cells

AAG 3 250nM

| Sample ID | Structure |
|---|---|
| AAG3 | 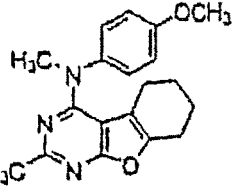 |
| AAG13 | 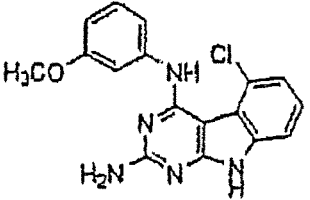 |
Figure 3

Figure 4. Biological Effects of AG Series of Compounds

| Sample ID | IC50 (MDA MB 435) ± SD | IC50 (SKOV3) ± SD (Sensitive) | IC50 (SKOV3M6/6) ± SD (Resistant) | Relative Resistance Value | EC50 for Microtubule Depolymerization |
|---|---|---|---|---|---|
| AAG 3 | 23.3 nM ± 1.9 | 40.0 nM ± 0.4 | 38.7 nM ± 3.5 | 1 | 60.8 nM |
| AAG 13 | 280 nM ± 0.1 | | | | 2.2 µM |
| Combrestatin A4 | 2.8 nM ± 0.2 | 4.5 nM ± 0.2 | 6.6 nM ± 1.3 | 1.5 | |
| Taxol® | 2.1 nM ± 0.7 | 2.2 nM ± 0.9 | 4.4 µM ± 0.9 | 2013 | |

National Cancer Institute Developmental Therapeutics Program In-Vitro Testing Results

| | Time | | | Log 10 Concentration Mean Optical Densities | | | |
|---|---|---|---|---|---|---|---|
| Panel/Cell Line | Zero | Ctrl | -8.0 | -7.0 | -6.0 | -5.0 | -4.0 |
| Leukemia | | | | | | | |
| CCRF-CEM | 0.185 | 0.828 | 0.817 | 0.172 | 0.170 | 0.167 | 0.166 |
| HL-60(TB) | 0.458 | 1.916 | 1.720 | 0.484 | 0.450 | 0.442 | 0.510 |
| K-562 | 0.176 | 1.273 | 1.200 | 0.456 | 0.415 | 0.402 | 0.186 |
| MOLT-4 | 0.336 | 1.397 | 1.401 | 0.612 | 0.525 | 0.530 | 0.567 |
| RPMI-8226 | 0.245 | 0.404 | 0.419 | 0.152 | 0.105 | 0.098 | 0.115 |
| SR | 0.359 | 0.927 | 0.856 | 0.495 | 0.459 | 0.423 | 0.255 |
| Non-Small Cell Lung Cancer | | | | | | | |
| A549/ATCC | 0.193 | 1.170 | 1.116 | 0.363 | 0.299 | 0.305 | 0.283 |
| EKVX | 0.483 | 1.270 | 1.265 | 0.802 | 0.764 | 0.816 | 0.742 |
| HOP-62 | 0.651 | 1.553 | 1.392 | 1.018 | 0.911 | 0.886 | 0.849 |
| NCI-H226 | 0.718 | 1.260 | 1.196 | 0.853 | 0.714 | 0.643 | 0.672 |
| NCI-H23 | 0.453 | 1.205 | 1.183 | 0.669 | 0.568 | 0.526 | 0.512 |
| NCI-H322M | 0.651 | 1.500 | 1.519 | 1.031 | 1.027 | 1.142 | 1.146 |
| NCI-H460 | 0.315 | 2.363 | 2.454 | 0.362 | 0.292 | 0.335 | 0.312 |
| NCI-H522 | 0.355 | 1.058 | 0.633 | 0.245 | 0.211 | 0.184 | 0.193 |
| Colon Cancer | | | | | | | |
| COLO 205 | 0.288 | 0.827 | 0.804 | 0.149 | 0.065 | 0.046 | 0.028 |
| HCC-2998 | 0.622 | 2.034 | 1.907 | 0.680 | 0.720 | 0.702 | 0.526 |
| HCT-116 | 0.162 | 1.305 | 1.209 | 0.109 | 0.109 | 0.093 | 0.093 |
| HCT-15 | 0.185 | 0.990 | 0.883 | 0.182 | 0.140 | 0.146 | 0.146 |
| HT29 | 0.127 | 1.107 | 1.063 | 0.281 | 0.399 | 0.233 | 0.244 |
| KM12 | 0.239 | 0.041 | 0.772 | 0.200 | 0.128 | 0.151 | 0.146 |
| SW-620 | 0.194 | 1.132 | 0.977 | 0.327 | 0.298 | 0.318 | 0.307 |
| CNS Cancer | | | | | | | |
| SF-268 | 0.355 | 1.027 | 0.964 | 0.431 | 0.309 | 0.310 | 0.281 |
| SF-295 | 0.543 | 1.387 | 1.002 | 0.456 | 0.374 | 0.421 | 0.497 |
| SF-539 | 0.667 | 1.842 | 1.764 | 0.424 | 0.354 | 0.407 | 0.462 |
| SNB-19 | 0.535 | 1.318 | 1.230 | 0.662 | 0.604 | 0.726 | 0.693 |
| SNB-75 | 0.450 | 1.007 | 0.925 | 0.605 | 0.633 | 0.650 | 0.691 |
| U251 | 0.270 | 1.233 | 1.200 | 0.305 | 0.238 | 0.245 | 0.209 |
| Melanoma | | | | | | | |
| LOX IMVI | 0.281 | 1.474 | 1.408 | 0.553 | 0.350 | 0.435 | 0.395 |
| MALME-3M | 0.505 | 0.030 | 0.922 | 0.687 | 0.671 | 0.679 | 0.718 |
| M14 | 0.301 | 1.314 | 1.176 | 0.378 | 0.344 | 0.351 | 0.392 |
| SK-MEL-28 | 0.303 | 0.741 | 0.624 | 0.471 | 0.470 | 0.441 | 0.399 |
| SK-MEL-5 | 0.411 | 2.090 | 2.163 | 0.590 | 0.118 | 0.183 | 0.155 |
| UACC-257 | 0.046 | 1.943 | 1.057 | 1.545 | 1.408 | 1.466 | 1.496 |
| UACC-62 | 0.544 | 1.759 | 1.302 | 0.706 | 0.840 | 0.820 | 0.766 |
| Ovarian Cancer | | | | | | | |
| OVCAR-3 | 0.191 | 0.657 | 0.591 | 0.168 | 0.147 | 0.181 | 0.191 |
| OVCAR-4 | 0.352 | 1.209 | 1.171 | 0.743 | 0.685 | 0.629 | 0.572 |
| OVCAR-5 | 0.516 | 1.206 | 1.165 | 0.740 | 0.692 | 0.816 | 0.408 |
| OVCAR-8 | 0.330 | 1.622 | 1.529 | 0.524 | 0.444 | 0.492 | 0.567 |
| SK-OV-3 | 0.430 | 0.817 | 0.884 | 0.411 | 0.380 | 0.359 | 0.353 |
| Renal Cancer | | | | | | | |
| 786-0 | 0.650 | 2.159 | 2.110 | 1.106 | 0.814 | 0.705 | 0.822 |
| A498 | 0.751 | 1.352 | 1.205 | 0.600 | 0.539 | 0.682 | 0.706 |
| ACHN | 0.304 | 1.196 | 1.152 | 0.578 | 0.466 | 0.453 | 0.419 |
| CAKI-1 | 0.424 | 0.544 | 0.508 | 0.352 | 0.322 | 0.322 | 0.377 |
| SN12C | 0.337 | 1.187 | 1.155 | 0.580 | 0.537 | 0.530 | 0.433 |
| TK-10 | 0.479 | 1.144 | 1.052 | 0.885 | 0.800 | 0.816 | 0.762 |
| UO-31 | 0.374 | 1.230 | 1.086 | 0.693 | 0.628 | 0.544 | 0.550 |
| Prostate Cancer | | | | | | | |
| DU-145 | 0.274 | 0.967 | 0.929 | 0.368 | 0.251 | 0.273 | 0.305 |
| Breast Cancer | | | | | | | |
| MCF7 | 0.288 | 1.373 | 1.245 | 0.349 | 0.299 | 0.324 | 0.322 |
| NCI/ADR-RES | 0.388 | 1.487 | 1.247 | 0.329 | 0.363 | 0.346 | 0.295 |
| MDA-MB-231/ATCC | 0.464 | 1.159 | 1.198 | 0.505 | 0.451 | 0.412 | 0.476 |
| HS 578T | 0.430 | 0.898 | 0.736 | 0.397 | 0.420 | 0.389 | 0.377 |
| MDA-MB-435 | 0.361 | 1.177 | 0.730 | 0.097 | 0.121 | 0.181 | 0.293 |
| BT-549 | 0.859 | 1.660 | 1.545 | 1.097 | 0.983 | 0.850 | 0.875 |
| T-47D | 0.324 | 0.679 | 0.643 | 0.474 | 0.551 | 0.549 | 0.504 |
| MDA-MB-468 | 0.995 | 2.599 | 2.416 | 1.449 | 1.259 | 1.157 | 1.339 |

Figure 5a

National Cancer Institute Developmental Therapeutics Program In-Vitro Testing Results

| Panel/Cell Line | Percent Growth | | | | | Log 10 Concentration | | |
|---|---|---|---|---|---|---|---|---|
| | -8.0 | -7.0 | -6.0 | -5.0 | -4.0 | GI50 | TGI | LC50 |
| Leukemia | | | | | | | | |
| CCRF-CEM | 98 | -7 | -8 | -10 | -11 | 2.88E-8 | 8.58E-8 | > 1.00E-4 |
| HL-60(TB) | 87 | 2 | -2 | -3 | 4 | 2.70E-8 | , | > 1.00E-4 |
| K-562 | 93 | 26 | 22 | 21 | 1 | 4.36E-8 | > 1.00E-4 | > 1.00E-4 |
| MOLT-4 | 100 | 26 | 18 | 19 | 22 | 4.76E-8 | > 1.00E-4 | > 1.00E-4 |
| RPMI-8226 | 73 | -38 | -57 | -60 | -53 | 1.60E-8 | 4.54E-8 | 4.18E-7 |
| SR | 88 | 24 | 17 | 11 | -29 | 3.09E-8 | 1.91E-5 | > 1.00E-4 |
| Non-Small Cell Lung Cancer | | | | | | | | |
| A549/ATCC | 94 | 17 | 11 | 11 | 9 | 3.77E-8 | > 1.00E-4 | > 1.00E-4 |
| EKVX | 99 | 41 | 36 | 42 | 33 | 6.90E-8 | > 1.00E-4 | > 1.00E-4 |
| HOP-62 | 82 | 41 | 29 | 26 | 22 | 5.95E-8 | > 1.00E-4 | > 1.00E-4 |
| NCI-H226 | 87 | 24 | -1 | -11 | -6 | 3.90E-8 | 9.50E-7 | > 1.00E-4 |
| NCI-H23 | 88 | 26 | 14 | 9 | 7 | 4.06E-8 | > 1.00E-4 | > 1.00E-4 |
| NCI-H322M | 91 | 40 | 40 | 52 | 52 | | > 1.00E-4 | > 1.00E-4 |
| NCI-H460 | 105 | 2 | -7 | 1 | -1 | 3.41E-8 | , | > 1.00E-4 |
| NCI-H522 | 40 | -31 | -41 | -48 | -46 | < 1.00E-8 | 3.64E-8 | > 1.00E-4 |
| Colon Cancer | | | | | | | | |
| COLO 205 | 96 | -48 | -77 | -84 | -80 | 2.07E-8 | 4.61E-8 | 1.13E-7 |
| HCC-2998 | 91 | 4 | 8 | 6 | -15 | 2.95E-8 | 1.85E-5 | > 1.00E-4 |
| HCT-116 | 98 | 4 | -29 | -39 | -39 | 3.26E-8 | 1.33E-7 | > 1.00E-4 |
| HCT-15 | 87 | 2 | -25 | -22 | -22 | 2.60E-8 | 9.59E-8 | > 1.00E-4 |
| HT29 | 95 | 16 | 17 | 11 | 12 | 3.71E-8 | > 1.00E-4 | > 1.00E-4 |
| KM12 | 89 | -17 | -46 | -37 | -39 | 2.33E-8 | 6.96E-8 | > 1.00E-4 |
| SW-620 | 83 | 14 | 11 | 13 | 12 | 3.04E-8 | > 1.00E-4 | > 1.00E-4 |
| CNS Cancer | | | | | | | | |
| SF-268 | 91 | 11 | -13 | -11 | -21 | 3.26E-8 | 2.91E-7 | > 1.00E-4 |
| SF-295 | 54 | -16 | -31 | -23 | -9 | 1.15E-8 | 5.92E-8 | > 1.00E-4 |
| SF-539 | 93 | -37 | -47 | -39 | -31 | 2.16E-8 | 5.23E-8 | > 1.00E-4 |
| SNB-19 | 89 | 16 | 15 | 24 | 20 | 3.42E-8 | > 1.00E-4 | > 1.00E-4 |
| SNB-75 | 85 | 28 | 33 | 36 | 43 | 4.14E-8 | > 1.00E-4 | > 1.00E-4 |
| U251 | 97 | 4 | -11 | -9 | -23 | 3.17E-8 | 1.74E-7 | > 1.00E-4 |
| Melanoma | | | | | | | | |
| LOX IMVI | 94 | 23 | 6 | 13 | 10 | 4.17E-8 | > 1.00E-4 | > 1.00E-4 |
| MALME-3M | 98 | 43 | 39 | 41 | 50 | , | > 1.00E-4 | > 1.00E-4 |
| M14 | 86 | 8 | 4 | 5 | 9 | 2.89E-8 | > 1.00E-4 | > 1.00E-4 |
| SK-MEL-2B | 73 | 38 | 38 | 32 | 22 | 4.62E-8 | > 1.00E-4 | > 1.00E-4 |
| SK-MEL-5 | 104 | 11 | -71 | -55 | -62 | 3.80E-8 | 1.35E-7 | 5.50E-7 |
| UACC-257 | 91 | 60 | 46 | 52 | 55 | , | > 1.00E-4 | > 1.00E-4 |
| UACC-62 | 62 | 20 | 24 | 23 | 18 | 1.95E-8 | > 1.00E-4 | > 1.00E-4 |
| Ovarian Cancer | | | | | | | | |
| OVCAR-3 | 86 | -12 | -23 | -5 | , | 2.32E-8 | 1.00E-4 | > 1.00E-4 |
| OVCAR-4 | 95 | 46 | 39 | 32 | 26 | 8.17E-8 | > 1.00E-4 | > 1.00E-4 |
| OVCAR-5 | 94 | 34 | 25 | 14 | -5 | 5.35E-8 | 5.33E-5 | > 1.00E-4 |
| OVCAR-8 | 93 | 15 | 9 | 12 | 18 | 3.65E-8 | > 1.00E-4 | > 1.00E-4 |
| SK-OV-3 | 93 | -4 | -12 | -17 | -18 | 2.77E-8 | 9.01E-8 | > 1.00E-4 |
| Renal Cancer | | | | | | | | |
| 786-0 | 96 | 30 | 10 | 8 | 11 | 4.92E-8 | > 1.00E-4 | > 1.00E-4 |
| A498 | 87 | -8 | -15 | -9 | -6 | 2.46E-8 | 8.17E-8 | > 1.00E-4 |
| ACHN | 95 | 31 | 18 | 17 | 13 | 5.01E-8 | > 1.00E-4 | > 1.00E-4 |
| CAKI-1 | 70 | -17 | -24 | -24 | -11 | 1.70E-8 | 6.38E-8 | > 1.00E-4 |
| SN12C | 95 | 29 | 23 | 23 | 11 | 4.83E-8 | > 1.00E-4 | > 1.00E-4 |
| TK-10 | 86 | 61 | 50 | 51 | 43 | , | > 1.00E-4 | > 1.00E-4 |
| UO-31 | 83 | 37 | 30 | 20 | 22 | 5.27E-8 | > 1.00E-4 | > 1.00E-4 |
| Prostate Cancer | | | | | | | | |
| DU-145 | 94 | 12 | -9 | -1 | 5 | 3.46E-8 | | > 1.00E-4 |
| Breast Cancer | | | | | | | | |
| MCF7 | 88 | 6 | 1 | 3 | 3 | 2.91E-8 | > 1.00E-4 | > 1.00E-4 |
| NCI/ADR-RES | 78 | -15 | -1 | -11 | -24 | 2.00E-8 | 6.87E-8 | > 1.00E-4 |
| MDA-MB-231/ATCC | 106 | 17 | -3 | -11 | 2 | 4.26E-8 | , | > 1.00E-4 |
| HS 578T | 74 | -10 | -4 | -11 | -14 | 1.95E-8 | 7.67E-8 | > 1.00E-4 |
| MDA-MB-435 | 45 | -73 | -67 | -50 | -19 | < 1.00E-8 | 2.41E-8 | |
| BT-549 | 85 | 29 | 14 | -2 | 13 | 4.22E-8 | , | > 1.00E-4 |
| T-47D | 90 | 42 | 64 | 63 | 51 | | > 1.00E-4 | > 1.00E-4 |
| MDA-MB-468 | 89 | 28 | 15 | 11 | 21 | 4.36E-8 | > 1.00E-4 | > 1.00E-4 |

Figure 5b

National Cancer Institute Developmental Therapeutics Program Mean Graphs

National Cancer Institute Developmental Therapeutics Program Mean Graphs

National Cancer Institute Developmental Therapeutics Program Mean Graphs

TRICYCLIC COMPOUNDS HAVING ANTIMITOTIC AND/OR ANTITUMOR ACTIVITY AND METHODS OF USE THEREOF

CROSS-REFERENCE TO RELATED APPLICATION

This application is a divisional utility patent application claiming priority to U.S. patent application Ser. No. 15/795,801, filed on Oct. 27, 2017, which is a divisional patent application claiming priority to U.S. patent application Ser. No. 15/283,705, filed on Oct. 3, 2016, now U.S. Pat. No. 9,802,955, granted Oct. 31, 2017, which is a divisional patent application claiming priority to U.S. patent application Ser. No. 14/719,824, filed on May 22, 2015, now U.S. Pat. No. 9,458,167, granted Oct. 4, 2016, which is a divisional patent application claiming priority to U.S. patent application Ser. No. 13/151,536, filed Jun. 2, 2011, now U.S. Pat. No. 9,056,869, granted Jun. 16, 2015, which is a continuation utility patent application claiming priority to U.S. patent application Ser. No. 12/170,633, filed on Jul. 10, 2008, now U.S. Pat. No. 7,982,035, granted Jul. 19, 2011, which is a continuation-in-part application claiming priority to U.S. patent application Ser. No. 11/845,143, filed Aug. 27, 2007, now U.S. Pat. No. 7,960,400, granted Jun. 14, 2011, having the same named inventor, Aleem Gangjee. The contents of U.S. patent application Ser. Nos. 11/845,143, 12/170,633, 13/151,536, 14/719,824, 15/283,705, and 15/795,801 are incorporated by reference in their entireties herein.

FIELD OF THE INVENTION

The present invention relates to tricyclic heteroaromatic compounds and their methods of use and, more particularly, to tricyclic heteroaromatic compounds that are antitumor agents that inhibit the function of microtubules (antimitotic agents or mitotic inhibitors) and that have antitumor activity. These tricyclic heteroaromatic compounds inhibit P-glycoprotein (Pgp) infected tumor cells, and inhibit paclitaxel sensitive and resistant tumor cells. The compounds may be made into acid salts that are water soluble for providing orally active antitumor agents.

BACKGROUND OF THE INVENTION

Mitosis is the process of nuclear division in eukaryotic cells that produces two daughter cells from one parent cell. The daughter cells and the original parent cell have identical chromosomes and DNA. Generally, cancer is a disease of mitosis. It is believed that cancer begins when a single cell is converted from a normal cell to a cancer cell. This is often due to a change in function of one or more genes that normally function to control cell growth. The cancer cells proliferate by repeated and uncontrolled mitosis, in contrast to normal cells which undergo only about 20 to 50 generations of replication and then cease. A tumor may be thought of as a mass of unhealthy cells that are dividing and growing in an uncontrolled way.

Microtubules are long, protein polymers that are hollow, tube-like filaments found in certain cell components such as the mitotic spindle. Each microtubule is composed of repeating subunits of the protein tubulin. Microtubules aggregate to form spindle fibers. During mitosis, cells use their spindle fibers to line up chromosomes, make copies of them, and divide into new cells with each new daughter cell having a single set of chromosomes. The polymerization dynamics of microtubules play a pivotal role in this process as part of cell replication. The crucial involvement of microtubules in mitosis makes them a target for antitumor agents. Antitumor agents that inhibit the function of microtubules are known as antimitotic agents.

Many classes of antimitotic agents are known. One such class is the vinca alkaloids exemplified by vincristine, vinblastine, vindesine, and vinorelbine. The vinca alkaloids are used in the treatment of leukemias, lymphomas, and small cell lung cancer. Another class of antimitotic agents are the taxanes, exemplified by paclitaxel (commercially available from Bristol-Myers Squibb Company under the tradename TAXOL) and docetaxel. The taxanes are useful in the treatment of breast, lung, ovarian, head and neck, and bladder carcinomas. Colchicine typifies another class of antimitotic agents. Colchicine, while not used as an antitumor agent, is a microtubule polymerization inhibitor. Lastly, the combrestatins are another class of antitumor agents. Antimitotic agents such as the vinca alakaloids, colchicine, colcemid, and nocadazol block mitosis by keeping the mitotic spindle from being formed. These agents bind to the tubulin and inhibit polymerization, preventing cells from making the spindles they need to move chromosomes around as they divide. In contrast, paclitaxel binds to the tubulin protein of microtubules, locking the microtubules in place and inhibiting their depolymerization. With the mitotic spindle still in place, a cell may not divide into daughter cells.

Multidrug or multiple drug resistance (MDR) is a major drawback of cancer chemotherapy. Ultimate failure of chemotherapy often times occurs with the use of antimitotic agents due to MDR. MDR may be inherently expressed by some tumor types while others acquire MDR after exposure to chemotherapy. P-glycoprotein (Pgp) is a 170 kilodalton (kDa) protein that belongs to the ATP-binding cassette superfamily of transporters. Pgp has been implicated as a primary cause of MDR in tumors. Pgps are efflux transporters found in the gut, gonads, kidneys, biliary system, brain, and other organs. A series of homologous proteins termed multidrug-resistance proteins (MRPs) are also known. MRPs are associated with MDR in tumors. The first MRP termed MRP1 was identified in a drug resistant lung cancer cell line that expressed Pgp. All of these transporters bind drugs within cells and release them to the extracellular space using ATP. Tumor cells pre-exposed to cytotoxic compounds often allow the cells to manifest resistance in the presence of the cytotoxic drug. Overexpression of Pgp has been reported in a number of tumor types, particularly after the patient has received chemotherapy, indicating the clinical importance of Pgp in MDR. The clinical significance of Pgp along with its limited expression in normal tissues makes Pgp a viable target for inhibition to reverse MDR.

While antimitotic agents have shown to be some of the most successful agents against malignancies, resistance, both intrinsic and acquired, often results in treatment failures. Thus, there exists a need to develop new compounds that possess antimitotic activity, anti-multidrug resistance activity, and antitumor activity, that may be used alone as a single agent in the treatment of cancer, or in combination with chemotherapeutic agents, including antimitotic agents, that shall inhibit mitosis in a wide variety of cells, including cells that are subject to MDR. There is a need, therefore, for single compounds which provide the desired antimitotic, anti-multidrug resistance and antitumor activities with a

SUMMARY OF THE INVENTION

The present invention meets the above need by providing tricyclic compounds having antimitotic activity, anti-multidrug resistance activity (for example, Pgp inhibition), and antitumor activity in a single molecule so that significant drawbacks of different aspects of drug transport of two or more drugs to their targets, additive or synergistic toxicities of two or more different drugs, resistance of cancer cells to a particular drug, as well as the cost associated with two or more drugs, is circumvented.

The present invention provides single compounds that exhibit antimitotic activity, anti-multidrug resistance activity (for example, Pgp inhibition), and antitumor activity in tumor cells, such as, without limitation, leukemia, non-small cell lung cancer, colon cancer, central nervous system cancer, melanoma, ovarian cancer, renal cancer, prostate cancer and breast cancer; and other proliferative diseases and disorders.

The present invention provides single compounds having a combinatorial chemotherapeutic potential of antimitotic activity, anti-multidrug resistance activity, and antitumor activity, and which inhibit paclitaxel sensitive and resistant tumor cells.

In an aspect of the present invention, there is provided a compound of Formula I:

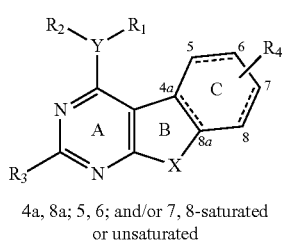

4a, 8a; 5, 6; and/or 7, 8-saturated
or unsaturated wherein both B and C rings may be completely or partially saturated or unsaturated with respect to bond 4a-8a, 5-6 and 7-8; the C ring may have an $R_4$ attached to the C ring at positions 5, 6, 7 or 8, or a combination of one or more of these positions depending on the saturation level of the C ring and wherein $R_4$ may be the same or different when attached to a plurality of the 5, 6, 7, or 8 positions of the C ring;

$R_1$ and $R_2$ each independently comprise one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

$R_1$ and $R_2$ are the same or different with the exception that $R_1$ and $R_2$ may not each be hydrogen at the same time;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

X comprises one of (a) a NH, (b) a $NR_5$, (c) an oxygen (O), (d) a sulfur (S), (e) a $CR_5$, and (f) a $CR_5R_{10}$, wherein $R_5$ and $R_{10}$ may be the same or different and comprise one of $R_1$; and Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent. Preferably, the compound of Formula I, as described herein, comprises pharmaceutically acceptable salts, prodrugs, solvates, or hydrates thereof.

In another embodiment of this invention the compound of Formula I, as described herein, further comprises wherein when the C ring is saturated or partially saturated, the substituted $R_4$ creates chirality when X is a C and $R_6$ and $R_7$ are different, then all stereoisomers thereof both separately and as racemic and/or diastereoisomeric mixtures are included.

In another aspect of the present invention, there is provided a compound of Formula II:

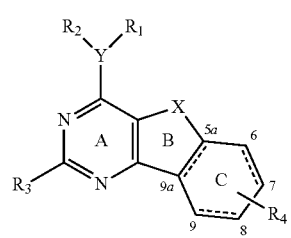

5a, 9a; 6, 7; and/or 8, 9-saturated
or unsaturated wherein both B and C rings may be completely or partially saturated or unsaturated with respect to bond 4a-8a, 5-6 and 7-8; the C ring may have an $R_4$ attached to the C ring at positions 5, 6, 7 or 8, or a combination of one or more of these positions depending on the saturation level of the C ring and wherein $R_4$ may be the same or different when attached to a plurality of the 5, 6, 7, or 8 positions of the C ring;

$R_1$ and $R_2$ each independently comprise one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

$R_1$ and $R_2$ are the same or different with the exception that $R_1$ and $R_2$ may not each be hydrogen at the same time;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

X comprises one of (a) a NH, (b) a $NR_5$, (c) an oxygen (O), (d) a sulfur (S), (e) a $CR_5$, and (f) a $CR_5R_{10}$, wherein $R_5$ and $R_{10}$ may be the same or different and comprise one of $R_1$; and Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e. is zero). Preferably, the compound of Formula II, as described herein, comprises pharmaceutically acceptable salts, prodrugs, solvates, or hydrates thereof.

In another embodiment of this invention the compound having Formula II, as described herein, further comprises wherein when the C ring is saturated or partially saturated, the substituted $R_4$ creates chirality when X is a C and $R_6$ and $R_7$ are different, then all stereoisomers thereof both separately and as racemic and/or diastereoisomeric mixtures are included.

In another embodiment of this invention, a method of treating a patient having cancer is provided comprising administering to the patient a therapeutically effective amount of a compound of Formula I, as described herein, or the salt, prodrug, solvate, or hydrate thereof.

In another embodiment of this invention, a method of treating a patient having cancer is provided comprising administering to the patient a therapeutically effective amount of a compound of Formula II, as described herein, or the salt, prodrug, solvate, or hydrate thereof.

In yet another embodiment of this invention, a method for inhibiting the mitosis of one or more cancerous cells is provided comprising subjecting one or more live cancerous cells to a mitotic inhibitory amount of a compound of Formula I, as described herein, or a pharmaceutically acceptable salt, prodrug, solvate, or hydrate of the compound of Formula I, for effecting the inhibition of mitosis of the cancerous cell(s).

Another embodiment of this invention provides a method for inhibiting the mitosis of one or more cancerous cells comprising subjecting at least one live cancerous cells to a mitotic inhibitory amount of a compound of Formula II, as described herein, or a pharmaceutically acceptable salt, prodrug, solvate, or hydrate of a compound of Formula II, for effecting the inhibition of mitosis of the cancerous cell(s).

BRIEF DESCRIPTION OF THE DRAWINGS

A full understanding of the invention can be gained from the following description of the preferred embodiments when read in conjunction with the accompanying drawings in which:

FIG. 3 shows the chemical structures of two compounds of the present invention, namely, Sample ID AAG3 and AAG 13.

FIG. 4 shows the biological effects of the compounds of the present invention.

FIG. 5a shows the results of the National Cancer Institute's preclinical in vitro tumor screening panel evaluating a compound of the present invention, namely, Sample ID AAG3.

FIG. 5b shows the results of the National Cancer Institute's preclinical in vitro tumor screening panel evaluating a compound of the present invention, namely, Sample ID AAG3.

DESCRIPTION OF THE PREFERRED EMBODIMENTS

Figure 1:
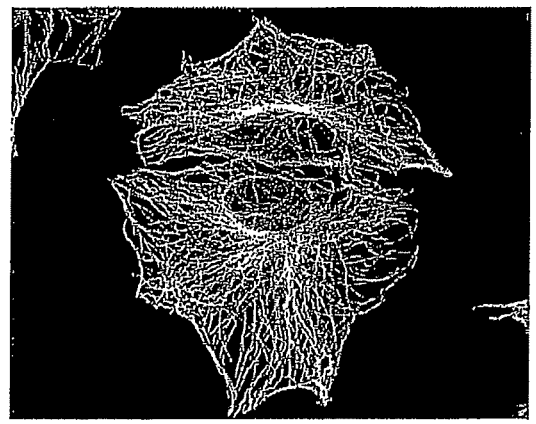
FIG. 1 show an immunofluorescence assay of A10 rat smooth muscle tumor cell line before treatment with a compound of the present invention (i.e. control).

The present invention provides tricyclic compounds having antimitotic activity, anti-multidrug resistance activity (for example, Pgp inhibition), and antitumor activity, and which inhibit paclitaxel sensitive and resistant tumor cells, in a single molecule and methods of use thereof.

The present invention provides a compound of the Formula I:

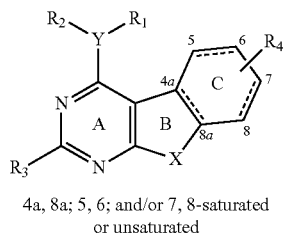

4a, 8a; 5, 6; and/or 7, 8-saturated
or unsaturated wherein both B and C rings may be completely or partially saturated or unsaturated with respect to bond 4a-8a, 5-6 and 7-8; the C ring may have an $R_4$ attached to the C ring at positions 5, 6, 7 or 8, or a combination of one or more of these positions depending on the saturation level of the C ring and wherein $R_4$ may be the same or different when attached to a plurality of the 5, 6, 7, or 8 positions of the C ring;

$R_1$ and $R_2$ each independently comprise one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

$R_1$ and $R_2$ are the same or different with the exception that $R_1$ and $R_2$ may not each be hydrogen at the same time;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

X comprises one of (a) a NH, (b) a $NR_5$, (c) an oxygen (O), (d) a sulfur (S), (e) a $CR_5$, and (f) a $CR_5R_{10}$, wherein $R_5$ and $R_{10}$ may be the same or different and comprise one of $R_1$; and Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e. is zero.)

In another embodiment of this invention the compound having Formula I, as described herein, further comprises wherein when the C ring is saturated or partially saturated, the substituted $R_4$ creates chirality when X is a C and $R_6$ and $R_7$ are different, then all stereoisomers thereof both separately and as a racemic and/or diastereoisomeric mixture(s) are included.

Compounds of the present invention, as described herein, may contain an asymmetric center and may thus exist as enantiomers. Where the compounds according to the present invention posses two or more asymmetric centers, they may additionally exist as diastereomers. The present invention includes all such possible stereoisomers as substantially pure resolved enantiomers, racemic mixtures thereof, and as mixtures of diastereomers. The formulas as described herein are shown without regard to a definitive stereochemistry at certain positions. The present invention includes all stereoisomers of such formulae and pharmaceutically acceptable salts thereof. Diastereoisomeric pairs of enantiomers may be separated by methods known by those skilled in the art, for example, fractional crystallization from a suitable solvent, and the pair of enantiomers thus obtained may be separated into individual stereoisomers by conventional means, known by those skilled in the art, for example by the use of an optically active acid or base as a resolving agent or on a chiral HPLC column. Further, any enantiomer or diastereomer of a compound of the formulae of the present invention may be obtained by stereospecific synthesis using optically pure starting materials or reagents of known configuration.

Preferably, the compounds of Formula I, as described herein, are pharmaceutically acceptable salts, prodrugs, solvates, or hydrates of the compound of Formula I.

Another embodiment of this invention provides a compound of Formula II:

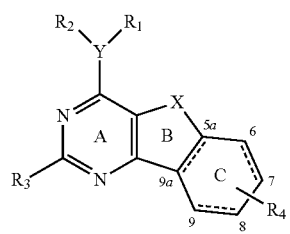

5a, 9a; 6, 7; and/or 8, 9-saturated
or unsaturated wherein both B and C rings may be completely or partially saturated or unsaturated with respect to bond 4a-8a, 5-6 and 7-8; the C ring may have an $R_4$ attached to the C ring at positions 5, 6, 7 or 8, or a combination of one or more of these positions depending on the saturation level of the C ring and wherein $R_4$ may be the same or different when attached to a plurality of the 5, 6, 7, or 8 positions of the C ring;

$R_1$ and $R_2$ each independently comprise one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

$R_1$ and $R_2$ are the same or different with the exception that $R_1$ and $R_2$ may not each be hydrogen at the same time;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

X comprises one of (a) a NH, (b) a $NR_5$, (c) an oxygen (O), (d) a sulfur (S), (e) a $CR_5$, and (f) a $CR_5R_{10}$, wherein $R_5$ and $R_{10}$ may be the same or different and comprise one of $R_1$; and Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e. is zero). Preferably, the compounds of Formula II are provided as pharmaceutically acceptable salts, prodrugs, solvates or hydrates thereof.

In another embodiment of this invention the compound having Formula II, as described herein, further comprises wherein when the C ring is saturated or partially saturated, the substituted $R_4$ creates chirality when X is a C and $R_6$ and $R_7$ are different, then all stereoisomers thereof both separately and as racemic and/or diastereoisomeric mixtures are included.

Other embodiments of the present invention provide pharmaceutically acceptable salts, solvates, and hydrates of the compounds of Formulae I and II. Preferably, the compounds of the present invention represented by Formulae I and II may be made into acid salts that are water soluble. Most preferably, these water soluble salts of Formulae I and II may be formulated into an oral dosage forms providing orally administered active antitumor agents. In the past, antimitotic agents have been plagued with water solubility problems, such as for example but not limited to Taxol® and combrestastatin, and a variety of solubilizing agents have been employed to improve their water solubility. The present salts of Formulae I and II overcome such water solubility problems and are generally completely water soluble.

In another embodiment of this invention, a method of treating a patient having cancer is provided comprising administering to the patient a therapeutically effective amount of a compound of Formula I, or a pharmaceutical acceptable salt, prodrug, solvate, or hydrate of the compound of Formula I:

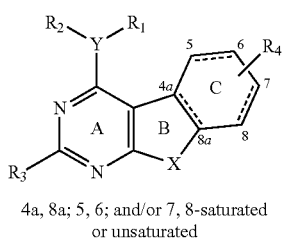

4a, 8a; 5, 6; and/or 7, 8-saturated or unsaturated wherein both B and C rings may be completely or partially saturated or unsaturated with respect to bond 4a-8a, 5-6 and 7-8; the C ring may have an $R_4$ attached to the C ring at positions 5, 6, 7 or 8, or a combination of one or more of these positions depending on the saturation level of the C ring and wherein $R_4$ may be the same or different when attached to a plurality of the 5, 6, 7, or 8 positions of the C ring;

$R_1$ and $R_2$ each independently comprise one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

$R_1$ and $R_2$ are the same or different with the exception that $R_1$ and $R_2$ may not each be hydrogen at the same time;

R₃ comprises one of (a) a hydrogen (H), (b) a halogen, (c) an alkyl having from one to ten carbon atoms and having a straight or a branched configuration, and wherein the alkyl is partially or completely saturated; (d) an NH₂, (e) an NHR₇, (f) an NR₇R₈, (g) an OH, (h) an OR, (i) an SH, and (j) an SR, and wherein R comprises one of R₁, and wherein R₇ and R₈ may be the same or different and comprise one of R₁;

R₄ comprises one of (a) R₁, (b) a halogen, (c) a mono-, di-, tri- or tetra-substituted alkyl, and (d) an alkyloxy, and wherein R₁ is H or a lower alkyl and R₂ is H or a lower alkyl then R₄ comprises one of (a) a NR₆R₇, (b) a SR₆, (c) a OR₆, and (d) a CHR₆R₇, wherein R₆ and R₇ may be the same or different and comprise one of R₁ and R₂;

X comprises one of (a) a NH, (b) a NR₅, (c) an oxygen (O), (d) a sulfur (S), (e) a CR₅, and (f) a CR₅R₁₀, wherein R₅ and R₁₀ may be the same or different and comprise one of R₁; and Y comprises one of (a) a nitrogen (N), (b) an oxygen (O), (c) a sulfur (S), and (d) a CR₆, wherein R₆ comprises one of R₁ and R₃, and wherein when Y comprises O or S then R₂ is absent (i.e. is zero).

As used herein, the term "patient" means members of the animal kingdom, including, but not limited to, human beings. As used herein, the term "having cancer" means that the patient has been diagnosed with cancer.

As used herein, the term "therapeutically effective amount" refers to that amount of any of the present compounds required to bring about a desired effect in a patient. The desired effect will vary depending on the illness being treated. For example, the desired effect may be reducing tumor size, destroying cancerous cells, and/or preventing metastasis, any one of which may be the desired therapeutic response. On its most basic level, a therapeutically effective amount is that amount needed to inhibit the mitosis of a cancerous cell or to facilitate the reversal of multidrug resistance, particularly, for example due to P-glycoprotein, (i.e. an effective mitotic inhibitory amount). Any amount of mitotic inhibition or reversal of multidrug resistance will yield a benefit to a patient and is therefore within the scope of the invention.

In another embodiment of this invention the method of treating a patient having cancer by administering to the patient a therapeutically effective amount of compound of Formula I, as described herein, further comprises wherein the compound of Formula I wherein the C ring is saturated or partially saturated, the substituted R₄ creates chirality when X is a C and R₆ and R₇ are different, then all stereoisomers thereof both separately and as racemic and/or diastereoisomeric mixtures are included.

In another embodiment of this invention, a method of treating a patient having cancer is provided comprising administering to the patient a therapeutically effective amount of a compound of Formula II, or a pharmaceutical acceptable salt, prodrug, solvate, or hydrate of the compound of Formula II:

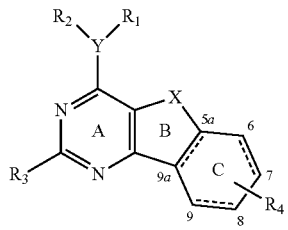

5a, 9a; 6, 7; and/or 8, 9-saturated or unsaturated wherein both B and C rings may be completely or partially saturated or unsaturated with respect to bond 4a-8a, 5-6 and 7-8; the C ring may have an R₄ attached to the C ring at positions 5, 6, 7 or 8, or a combination of one or more of these positions depending on the saturation level of the C ring and wherein R₄ may be the same or different when attached to a plurality of the 5, 6, 7, or 8 positions of the C ring;

R₁ and R₂ each independently comprise one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a CH₂ bridge, and wherein the substituent may be optionally partially or completely saturated or unsaturated when it is not represented by said halogen;

R₁ and R₂ are the same or different with the exception that R₁ and R₂ may not each be hydrogen at the same time;

R₃ comprises one of (a) a hydrogen (H), (b) a halogen, (c) an alkyl having from one to ten carbon atoms and having a straight or a branched configuration, and wherein the alkyl is partially or completely saturated; (d) an NH₂, (e) an NHR₇, (f) an NR₇R₈, (g) an OH, (h) an OR, (i) an SH, and (j) an SR, and wherein R comprises one of R₁, and wherein R₇ and R₈ may be the same or different and comprise one of R₁;

R₄ comprises one of (a) R₁, (b) a halogen, (c) a mono-, di-, tri- or tetra-substituted alkyl, and (d) an alkyloxy, and wherein R₁ is H or a lower alkyl and R₂ is H or a lower alkyl then R₄ comprises one of (a) a NR₆R₇, (b) a SR₆, (c) a OR₆, and (d) a CHR₆R₇, wherein R₆ and R₇ may be the same or different and comprise one of R₁ and R₂;

X comprises one of (a) a NH, (b) a NR$_5$, (c) an oxygen (O), (d) a sulfur (S), (e) a CR$_5$, and (f) a CR$_5$R$_{10}$, wherein R$_5$ and R$_{10}$ may be the same or different and comprise one of R$_1$; and Y comprises one of (a) a nitrogen (N), (b) an oxygen (O), (c) a sulfur (S), and (d) a CR$_6$, wherein R$_6$ comprises one of R$_1$ and R$_3$, and wherein when Y comprises O or S then R$_2$ is absent (i.e. is zero).

In another embodiment of the method for treating a patient having cancer by administering to the patient a therapeutically effective amount of a compound of the Formula II further comprises wherein the compound of Formula II wherein the C ring is saturated or partially saturated, the substituted R$_4$ creates chirality when X is a C and R$_6$ and R$_7$ are different, then all stereoisomers thereof both separately and as racemic and/or diastereoisomeric mixtures are included.

Compounds of the present invention covered under Formula I and II may also be administered with one or more additional treatment agents, i.e., a chemotherapeutic agent. Suitable candidates for the additional chemotherapeutic agent include for example but are not limited to, paclitaxel, docetaxel, vinca alkaloids, colchicines, colcemid, cisplatin, and nocadazol. The presence of the compound of the present invention shall enhance the effectiveness of the chemotherapeutic agent by facilitating the reversal of multidrug resistance, particularly due to Pgp, and at least partially restoring the sensitivity of tumors to antimitotic agents.

In yet another embodiment of this invention, a method for inhibiting the mitosis of one or more cancerous cells is provided comprising subjecting one or more live cancerous cells to an effective inhibitory amount of a compound of Formula I, or a salt, prodrug, solvate, or hydrate of a compound of Formula I:

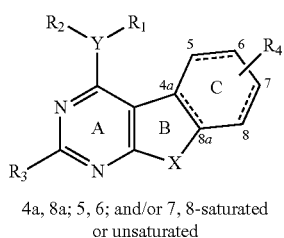

I 4a, 8a; 5, 6; and/or 7, 8-saturated
or unsaturated wherein both B and C rings may be completely or partially saturated or unsaturated with respect to bond 4a-8a, 5-6 and 7-8; the C ring may have an R$_4$ attached to the C ring at positions 5, 6, 7 or 8, or a combination of one or more of these positions depending on the saturation level of the C ring and wherein R$_4$ may be the same or different when attached to a plurality of the 5, 6, 7, or 8 positions of the C ring;

R$_1$ and R$_2$ each independently comprise one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a CH$_2$ bridge, and wherein the substituent may be optionally partially or completely saturated or unsaturated when it is not represented by said halogen;

R$_1$ and R$_2$ are the same or different with the exception that R$_1$ and R$_2$ may not each be hydrogen at the same time;

R$_3$ comprises one of (a) a hydrogen (H), (b) a halogen, (c) an alkyl having from one to ten carbon atoms and having a straight or a branched configuration, and wherein the alkyl is partially or completely saturated; (d) an NH$_2$, (e) an NHR$_7$, (f) an NR$_7$R$_8$, (g) an OH, (h) an OR, (i) an SH, and (j) an SR, and wherein R comprises one of R$_1$, and wherein R$_7$ and R$_8$ may be the same or different and comprise one of R$_1$;

R$_4$ comprises one of (a) R$_1$, (b) a halogen, (c) a mono-, di-, tri- or tetra-substituted alkyl, and (d) an alkyloxy, and wherein R$_1$ is H or a lower alkyl and R$_2$ is H or a lower alkyl then R$_4$ comprises one of (a) a NR$_6$R$_7$, (b) a SR$_6$, (c) a OR$_6$, and (d) a CHR$_6$R$_7$, wherein R$_6$ and R$_7$ may be the same or different and comprise one of R$_1$ and R$_2$;

X comprises one of (a) a NH, (b) a NR$_5$, (c) an oxygen (O), (d) a sulfur (S), (e) a CR$_5$, and (f) a CR$_5$R$_{10}$, wherein R$_5$ and R$_{10}$ may be the same or different and comprise one of R$_1$; and Y comprises one of (a) a nitrogen (N), (b) an oxygen (O), (c) a sulfur (S), and (d) a CR$_6$, wherein R$_6$ comprises one of R$_1$ and R$_3$, and wherein when Y comprises O or S then R$_2$ is absent (i.e. is zero), for effecting the inhibition of mitosis of the cancerous cells.

Another embodiment of this invention provides a method for inhibiting the mitosis of one or more cancerous cells comprising subjecting live cancerous cells to an effective mitotic inhibitory amount of a compound of Formula II, or a salt, prodrug, solvate, or hydrate of a compound of Formula II:

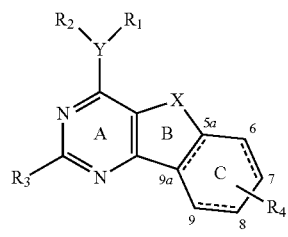

II 5a, 9a; 6, 7; and/or 8, 9-saturated
or unsaturated wherein both B and C rings may be completely or partially saturated or unsaturated with respect to bond 4a-8a, 5-6 and 7-8; the C ring may have an R$_4$ attached to the C ring at positions 5, 6, 7 or 8, or a combination of one or more of these positions depending on the saturation level of the C ring and wherein $R_4$ may be the same or different when attached to a plurality of the 5, 6, 7, or 8 positions of the C ring;

$R_1$ and $R_2$ each independently comprise one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

$R_1$ and $R_2$ are the same or different with the exception that $R_1$ and $R_2$ may not each be hydrogen at the same time;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

X comprises one of (a) a NH, (b) a $NR_5$, (c) an oxygen (O), (d) a sulfur (S), (e) a $CR_5$, and (f) a $CR_5R_{10}$, wherein $R_5$ and $R_{10}$ may be the same or different and comprise one of $R_1$; and Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e. is zero), for effecting the inhibition of mitosis of the cancerous cells.

As used herein, the term "lower alkyl" group refers to those lower alkyl groups having one to about ten carbon atoms, such as for example methyl, ethyl, propyl, butyl, pentyl, hexyl, cyclopropyl, cyclobutyl, cyclohexyl, cyclopropylmethyl or cyclobutylmethyl groups. Alkyl groups sharing one to about six carbon atoms are preferred. These lower alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

As used herein, the term "heteroalkyl" refers to alkyl chains from one to about 3 atoms where one or more of the carbons has been replaced with nitrogen, oxygen or sulfur, Thus "heteroalkyl" groups will include, for example, —$CH_2$—$CH_2$—NH—, —$CH_2$—S—, —S—$CH_2$—, —$CH_2$—O—, —$CH_2$—$CH_2$—O—, —O—$CH_2$—, —NH—$CH_2$—$CH_2$—, —N—CH=CH—, and other various combinations, as will be apparent to one skilled in the art. The above list is not meant to be exhaustive, and many combinations are contemplated as within the scope of the present invention.

The term "aryl" groups, as used herein, refers to compounds whose molecules have an aromatic ring structure, such as the six-carbon ring of benzene, or multiple rings which are either fused or unfused, such as condensed six-carbon rings of other aromatic derivatives. The term "aryl" is also defined to include diaryl, triaryl and polyaryl groups, which would have two, three or more rings, respectively. Thus, suitable aryl groups would include, for example, phenyl, biphenyl, naphthyl, phenanthrene, anthracene groups and aryl oxyaryl groups. This list is not meant to be exhaustive, and any aryl group, as these terms are defined above and commonly understood in the art, are within the scope of the present invention.

The term "heteroaryl" refers to aromatic ring structures having at least one atom in the ring which is not carbon, such as oxygen, nitrogen or sulfur. "Heteroaryls" as used herein also refers to aromatic ring structures that are part of larger ring structures, such as two or three member ring systems, which may be fused or unfused, in which one of the rings is as described above. Thus, "heteroaryl" refers to ring systems in which one or more rings contain a heteroatom and one or more rings do not. It will be understood that this list is not meant to be exhaustive, and that any heteroaryl group, as these terms are defined above and commonly understood in the art, are within the scope of the present invention. The heteroaryl ring systems may be fused ring systems or unfused. Examples of heteroaryl ring systems include, for example but are not limited to, pyridine, quinoline, isoquinoloine, pyrrole, thiophenes, furans, imidazoles, and the like, as well as fused ring structures having rings of different sizes, such as benzofurans, indoles, purines, and the like.

Also included within the scope of the present invention are alicyclic groups, as that term is understood in the art, and heterocyclic groups. As used herein, the term "heterocyclic group" refers to non-aromatic cyclic substituents in which one or more members of the ring is not carbon, and is at least one of an oxygen, sulfur or nitrogen atom, for example.

The terms "alkylaryl" (or "alkaryl") or "alkylheteroaryl" as used herein refer to groups having an alkyl moiety attached to an aryl or heteroaryl ring. The alkyl moiety is preferably a straight, branched or cyclic alkyl group having one to about six carbon atoms. This alkyl moiety may also contain oxygen, nitrogen or sulfur, and therefore may be an alkoxy group. The aryl or heteroaryl moiety of the alkylaryl group is a substituted or unsubstituted aryl or heteroaryl group, as these terms are described above. As used herein, the terms "alkylaryl" or "alkylheteroaryl" will also be used to refer to arylalkyl groups or heteroarylalkyl groups, as those terms are understood in the art, and denotes attachment of such a substituent at either the alkyl or the aryl portion of the group. Thus, for example, a benzyl group would be embraced by the term "alkylaryl".

Any of the cyclic substituents described above, such as the aryl, heteroaryl, alkylaryl, alkylheteroaryl, alicyclic, or heterocyclic groups are optionally substituted with one or more substituents as listed above. In the case of more than one substituent, the substituents are independently selected. "Alkoxy groups" and "alkyl groups" include straight or branched chains having up to about ten members. "Halogen" refers to chlorine, bromine, iodine and fluorine. "Aryl and heteroaryl groups" are as described above. When a carboxylic acid is a substituent, it will be appreciated that the moiety represents an acid such as benzoic acid.

As used herein, the terms "aroyl" or "heteroaroyl", such as when used within the term p-aroyl-L-glutamate, refers to benzoyl, napthoyl, thiophenoyl, furophenoyl, pyrroyl, and any other "aroyl" or "heteroaroyl" as these terms would be understood by one skilled in the art. "Aroyl" and "heteroaroyl" are generally defined in the art as an aromatic or heteroaromatic compound having a carbonyl moiety. As used herein, the term "glutamate" will be understood as representing both the ester form (glutamate) and the acid form (glutamic acid).

It will appreciated by those skilled in the art that a general formula depicting compounds having side chains with adjacent carbons having a double bond will result in both cis and trans isomers as possible structures. Both the cis and trans isomers, and mixtures thereof, of any such compound within the broad general formula described in Formulas I and II are contemplated as being within the scope of the present invention.

A preferred form of Formula I is shown in FIG. 3, Sample ID AAG3.

Proliferative diseases and/or disorders that may be treated according to the methods of the present invention include, without limitation, leukemia, non-small cell lung cancer, colon cancer, central nervous system (CNS) cancer, melanoma, ovarian cancer, renal cancer, prostate cancer, and breast cancer.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of a tricyclic compound of the present invention to produce the desired effect in association with a pharmaceutical carrier. The specification for the dosage unit forms of the invention are dictated by and directly dependent on the particular compound and the particular effect, or therapeutic response, that is desired to be achieved.

Compounds containing Formula I or Formula II, or pharmaceutically acceptable salts, prodrugs, solvates, or hydrates thereof, can be administered to a patient (an animal or human) via various routes including parenterally, orally or intraperitoneally. Parenteral administration includes the following routes that are outside the alimentary canal (digestive tract): intravenous; intramuscular; interstitial, intraarterial; subcutaneous; intraocular; intracranial; intraventricular; intrasynovial; transepithelial, including transdermal, pulmonary via inhalation, ophthalmic, sublingual and buccal; topical, including dermal, ocular, rectal, or nasal inhalation via insufflation or nebulization. Specific modes of administration shall depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered to a patient shall depend on the characteristics of the patient being treated, including for example, but not limited to, the patient's age, weight, health, and types and frequency of concurrent treatment, if any, of any other chemotherapeutic agent(s), all of which is determined by the clinician as one skilled in the art.

Compounds containing Formula I or Formula II, or a salt, a prodrug, a solvate, or a hydrate thereof, that are orally administered can be enclosed in hard or soft shell gelatin capsules, or compressed into tablets. Compounds also can be incorporated with an excipient and used in the form of ingestible tablets, buccal tablets, troches, capsules, sachets, lozenges, elixirs, suspensions, syrups, wafers and the like. Compounds containing Formula I or Formula II can be in the form of a powder or granule, a solution or suspension in an aqueous liquid or non-aqueous liquid, or in an oil-in-water emulsion.

The tablets, troches, pills, capsules and the like also can contain, for example, a binder, such as gum tragacanth, acacia, corn starch; gelating excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent. When the dosage unit form is a capsule, it can contain, in addition to the materials described above, a liquid carrier. Various other materials can be present as coatings or to otherwise modify the physical form of the dosage unit. For example, tablets, pills, or capsules can be coated with shellac, sugar or both. A syrup or elixir can contain the active compound, sucrose as a sweetening agent, methyl and propylparabens as preservatives, a dye and flavoring. Any material used in preparing any dosage unit form should be pharmaceutically pure and substantially non-toxic. Additionally, the compounds of Formula I or Formula II, and a salt thereof, can be incorporated into sustained-release preparations and formulations.

The compounds of Formula I or Formula II, or a salt, a prodrug, a solvate, or a hydrate thereof, can be administered to the central nervous system, parenterally or intraperitoneally. Solutions of the compound as a free base or a pharmaceutically acceptable salt can be prepared in water mixed with a suitable surfactant, such as hydroxypropylcellulose. Dispersions also can be prepared in glycerol, liquid polyethylene glycols and mixtures thereof, and in oils. Under ordinary conditions of storage and use, these preparations can contain a preservative and/or antioxidants to prevent the growth of microorganisms or chemical degeneration.

The pharmaceutical forms suitable for injectable use include, without limitation, sterile aqueous solutions or dispersions and sterile powders for the extemporaneous preparation of sterile injectable solutions or dispersions. In all cases, the form must be sterile and must be fluid to the extent that easy syringability exists. It can be stable under the conditions of manufacture and storage and must be preserved against the contaminating action of microorganisms, such as bacteria and fungi.

Compounds of the present invention may be contained within, mixed with, or associated with, a suitable (acceptable) pharmaceutical carrier for administration to a patient according to the particular route of administration desired. Suitable or acceptable pharmaceutical carriers refer to any pharmaceutical carrier that will solubilize the compounds of the present invention and that will not give rise to incompatability problems, and includes any and all solvents, dispersion media, coatings, antibacterial and antifungal agents, isotonic agents, absorption delaying agents, and the like. The use of such suitable or acceptable pharmaceutical carriers are well known by those skilled in the art. Preferred carriers include sterile water, physiologic saline, and five percent dextrose in water. Examples of other suitable or acceptable pharmaceutical carriers include, but are not limited to, ethanol, polyol (such as propylene glycol and liquid polyethylene glycol), suitable mixtures thereof, or vegetable oils. The proper fluidity can be maintained, for example, by the use of a coating, such as lecithin, by the maintenance of the required particle size (in the case of a dispersion) and by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the compound of Formula I or Formula II in the required amount in the appropriate solvent with various of the other ingredients enumerated above, as required, followed by filtered sterilization. Generally, dispersions are prepared by incorporating the sterilized compound of Formula I or Formula. II into a sterile vehicle that contains the basic dispersion medium and any of the other ingredients from those enumerated above. In the case of sterile powders for the preparation of sterile injectable solutions, the preferred methods of preparation are vacuum drying and freeze drying.

Pharmaceutical compositions which are suitable for administration to the nose and buccal cavity include, without limitation, self-propelling and spray formulations, such as aerosol, atomizers and nebulizers.

The therapeutic compounds of Formula I and Formula II, or a salt, a prodrug, a solvate, or a hydrate thereof, can be administered to a patient alone or in combination with pharmaceutically acceptable carriers or as pharmaceutically acceptable salts, the proportion of which is determined by the solubility and chemical nature of the compound, chosen route of administration to the patient and standard pharmaceutical practice.

The present invention is more particularly described in the following non-limiting examples, which are intended to be illustrative only, as numerous modifications and variations therein will be apparent to those skilled in the art.

EXAMPLES

Flow cytometric analysis was performed to assess the effect of the tricyclic compounds of the present invention on the cell cycle phase distributions of MDA MB 435 human breast cancer. The percentage of cells in the $G_2/M$ phases was increased approximately two-fold by treatment of the cells for twenty four hours with tricyclic compounds AAG3 and AAG13.

Figure 2:
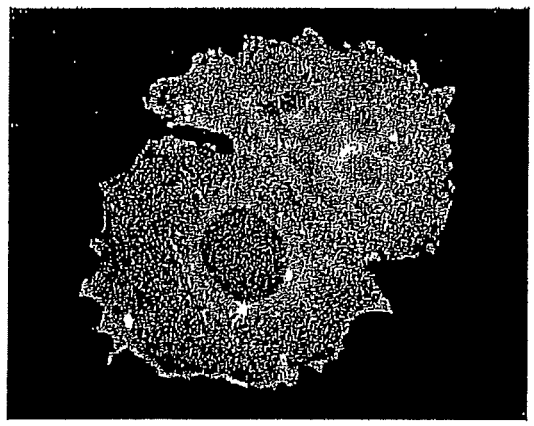
FIG. 2 shows a microtubule depolymerization immunofluorescence assay of A10 rat smooth muscle tumor cell line following treatment with a compound of the present invention, namely, Sample ID AAG3.

FIG. 1 shows a microtubule immunofluorescence assay of a A-10 rat smooth muscle cell line before treatment with a compound of this invention (i.e. control). FIG. 2 shows the microtubule depolymerization immunofluorescence assay of an A-10 rat smooth muscle cell line following treatment with the compound of the present invention AAG3. AAG3 has structural Formula I wherein $R_1$ is a methoxybenzyl group and $R_2$ and $R_3$ are each a methyl group and wherein ring C is saturated, and wherein X is an O. A-10 rat smooth muscle cells were used since they grow as flat monolayers that are amenable to imaging. The A-10 cells were treated for twenty four (24) hours (h) with EtOH (control), and 250nM (nanomolar) AAG3. Microtubules were then visualized by indirect immunofluorescence staining with beta-tubulin antibodies. The control cells shown in FIG. 1 displayed extensive microtubule systems with perimeter organizing centers. Treatment with AAG3 caused losses of microtubules in the cells. This immunofluorescence assay of FIG. 2 shows that AAG3 was effective in depolymerizing the tubulin protein microtubule of A-10 cells. The AAG3 compound has potent nanomolar tubulin inhibitory activity. Compounds of the present invention, having the structural Formulae I and II, as set forth herein, inhibit the microtubule dynamics. The inhibition of microtubule dynamics hinders microtubule formation and results in mitotic arrest and initiation of apoptosis or programmed cell death.

The biological effects of two of the compounds of the present invention, namely AAG3 and AAG13, as compared to known antimitotic agents Taxol® (Bristol-Myers Squibb Company) and combrestastatin A4, commercially available from Cayman Chemicals, Michigan, USA, are presented in FIG. 4. Antimitotic compounds AAG3, AAG 13, Taxol®, and combrestastatinA4, were evaluated for cytotoxity towards the panel of human cell lines MDA MB 435 (human breast cancer), SKOV3 (human ovarian cancer), and SKOV3M6/6 (Pgp infected human ovarian cancer). FIG. 4 shows the $IC_{50}$ of each of these antimitotic compounds towards each cancer cell line. The $IC_{50}$ is the inhibitory concentration required to effectuate fifty percent inhibition of cell growth. FIG. 4 shows that the compounds of the present invention, AAG3 and AAG13, have cytotoxic activity toward each of the human cancer cell lines tested. Although Taxol® and combrestastatin A4 were more potent than compound AAG3 in the MDA MB 435 and the SKOV3 sensitive cell lines, Taxol® was subject to tumor resistance due to the overexpression of P-glycoprotein (Pgp) in the ovarian cancer cell line SKOV3M6/6. FIG. 4 shows the IC50 values of 3.5 nanoM (nM) for AAG3 and 4.4 microM (µM) for Taxol® toward the Pgp infected human ovarian cancer cell line SKOV3M6/6. FIG. 4 shows the calculated relative resistance value of 1 for compound AAG3 and a relative resistance value of 2013 for Taxol®. Thus, the results confirm that overexpression of Pgp did not effect cell sensitivity to compound AAG3 of the present invention.

FIG. 5 shows the results of testing compound AAG3 (otherwise identified as XZ/AG/153-423 (73100)) of the present invention using National cancer Institute (NCI) 55 human tumor lines. The cells lines, which represent leukemia, non-small cell lung cancer, colon cancer, central nervous system cancer, melanoma, ovarian cancer, renal cancer, prostate cancer, and breast cancer, are listed in FIG. 5. Testing was in accordance with the NCI Developmental Therapeutics Program (DTP) In Vitro Cell Line Screening Project (IVCLSP). Methodology for testing under IVCLSP is provided at http://dtp.nci.gov/branches/btb/ivclsp.html.

FIG. 5 shows the tumor cell inhibitory activity, measured by $GI_{50}$ values ($10^{-8}$ M) for AAG3. $GI_{50}$ is the concentration of chemical required to reduce the growth of treated cells to half that of untreated cells (i.e. control). $GI_{50}$ represents the concentration of chemical required to effectuate fifty percent inhibition of cell growth. AAG3 exhibited $GI_{50}$ values of single digit $10^{-8}$ molar levels against all 55 tumor cell lines.

An NCI COMPARE analysis was performed for AAG3 to elucidate a possible mechanism of action by comparing responses of the 55 cell lines to known microtubule-targeting agents. For microtubule specific compounds, the cell type selectivity profile in tumor growth inhibitory (TGI) levels is highly indicative of the compound's mechanism of action. A TGI Correlation value that is equal to or greater than 0.6 is generally considered by those skilled in the art to be a good correlation value for classification as a microtubule targeting agent. The results of the NCI COMPARE analysis for compound AAG3 of the present invention is set forth in Table 1.

TABLE 1

TGI endpoint TARGET SET: STANDARD_AGENTS_TGI
SEED: S747156-4M TGI 2 days AVGDATA
SEED TYPE: NSC_FIVE_DOSE

| Rank | Vector | Correlation | Cell line |
|---|---|---|---|
| 1 | vincristine sulfate S67574-3M TGI 2 days AVGDATA | 0.675 | 49 |
| 2 | maytansine S 153858-4M TGI 2 days AVGDATA | 0.6 | 49 |
| 3 | vinblastine sulfate S49842-5.6M TGI 2 days AVGDATA | 0.53 | 49 |
| 4 | rhizoxin S332598-4M TGI 2 days AVGDATA | 0.52 | 49 |
| 5 | rhizoxin S332598-4M TGI 2 days AVGDATA | 0.467 | 47 |

The NCI COMPARE analysis was performed for AAG3 to elucidate a possible mechanism of action of AAG3 by the similarity response of the cell lines to known compounds. The four compounds that showed the best correlation with AAG3 are all well-known microtubule targeting agents. For microtubule specific compounds, the cell type selectivity profile in TGI (Total Growth Inhibition) level is highly indicative of the compounds mechanism of action. Thus AAG3 is a microtubule inhibitor. This COMPARE analysis also indicates that AAG3 acts most like vincristine sulfate (correlation 0.7), which is a well known anticancer agent widely used in the clinic and strongly suggests that AAG3 would be highly active in vivo. The tumor inhibitory data from the NCI preclinical tumor screen also strongly suggest in vivo activity for AAG3.

Figure 6A:
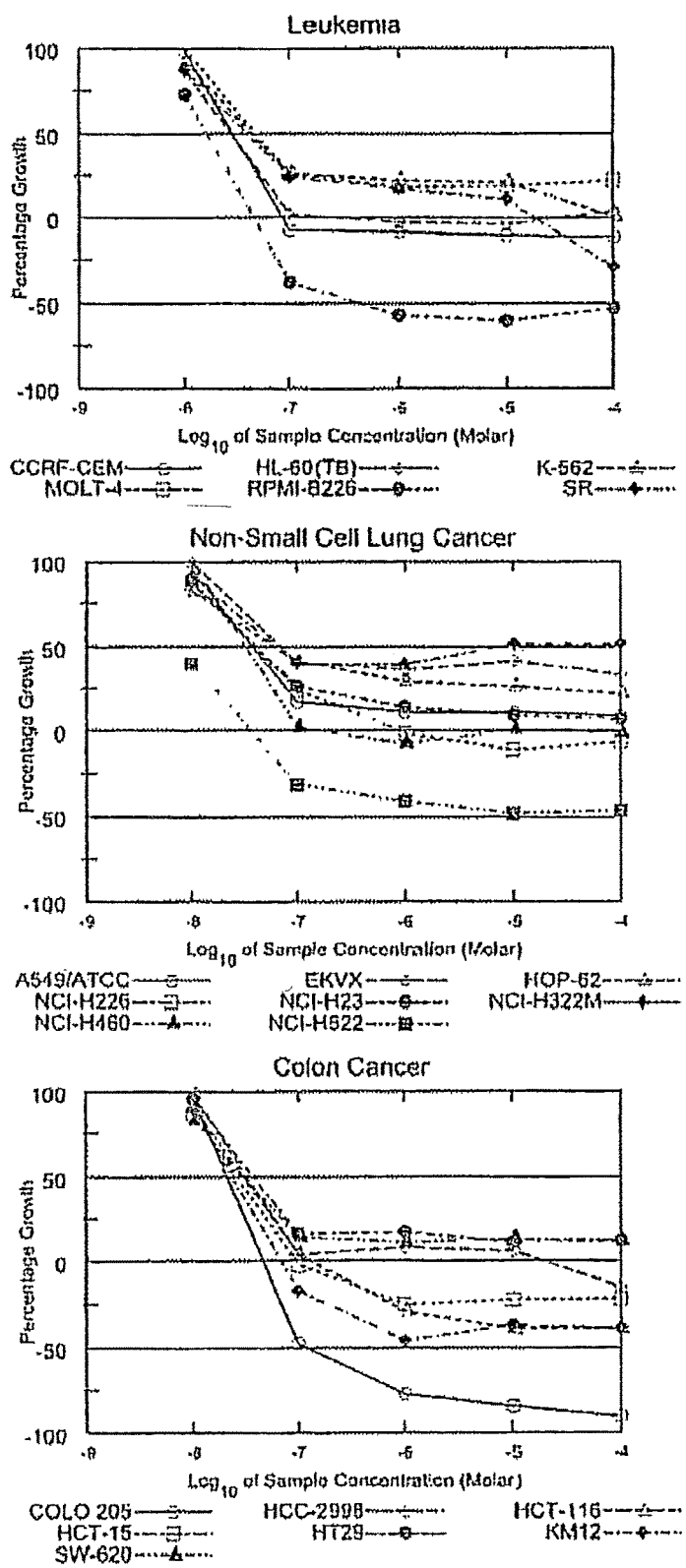
FIG. 6a shows individual dose response curves of percentage growth for the cancer cell lines set forth in FIG. 5.
Figure 6B:
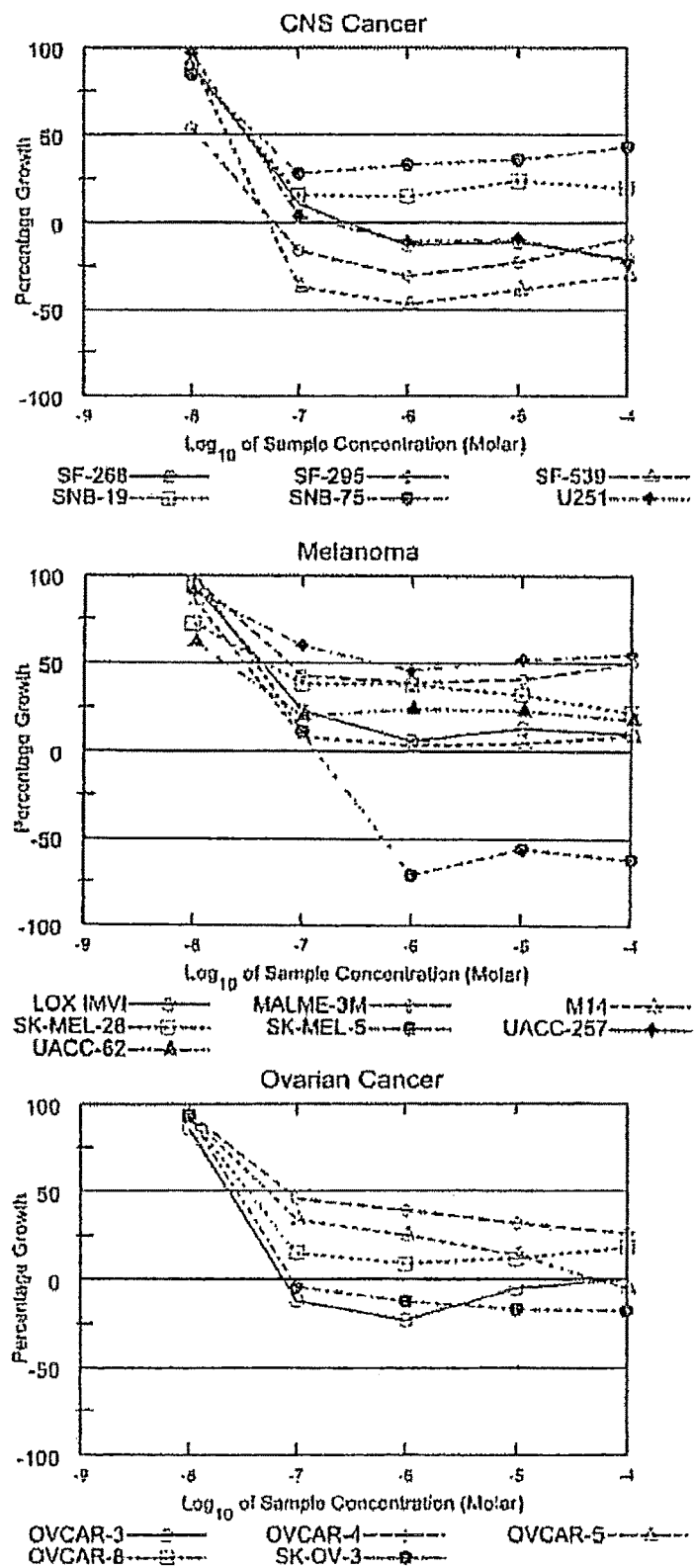
FIG. 6b shows individual dose response curves of percentage growth for the cancer cell lines set forth in FIG. 5.
Figure 6C:
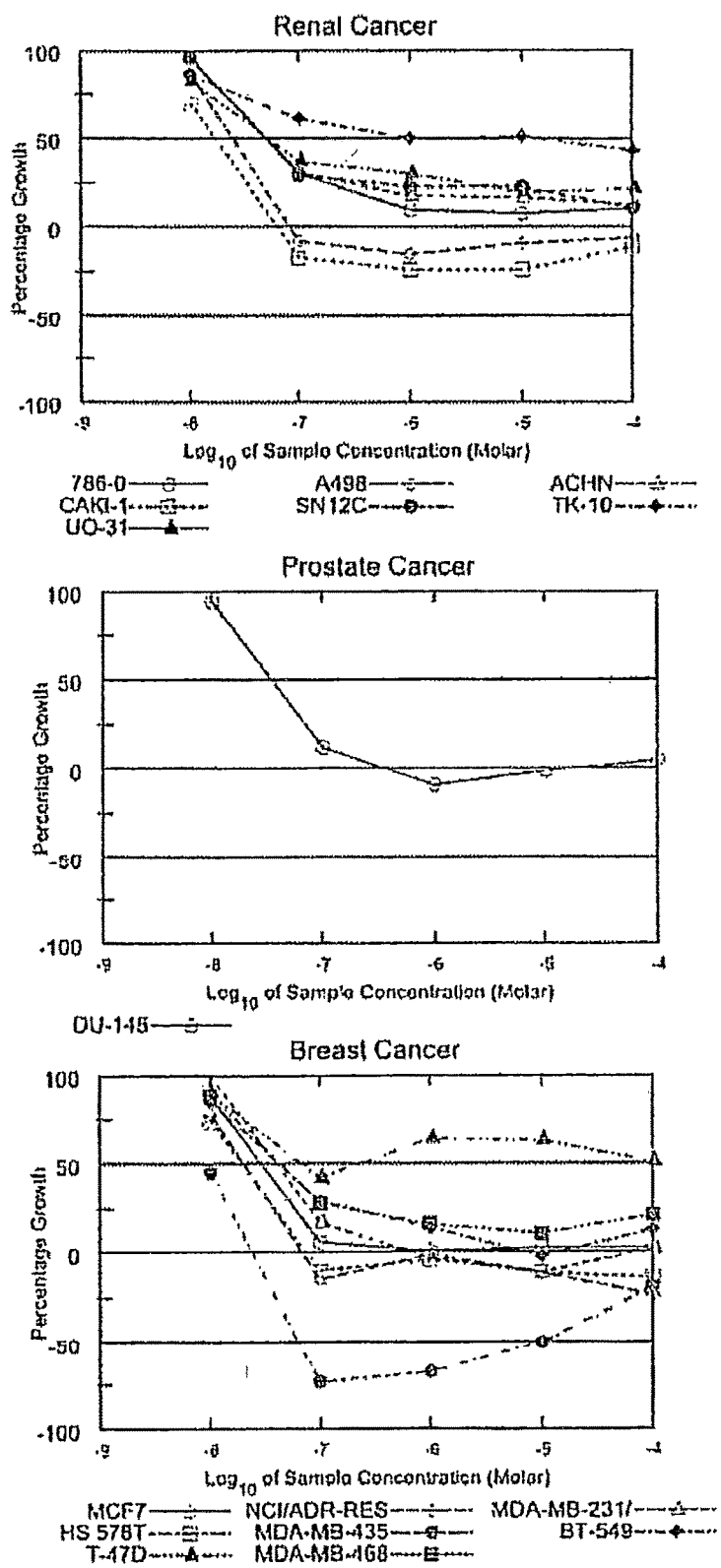
FIG. 6c shows individual dose response curves of percentage growth for the cancer cell lines set forth in FIG. 5.

FIGS. 6a, 6b, and 6c show individual dose response curves of percentage growth for each of the cancer cell lines set forth in FIG. 5.

Figure 7:
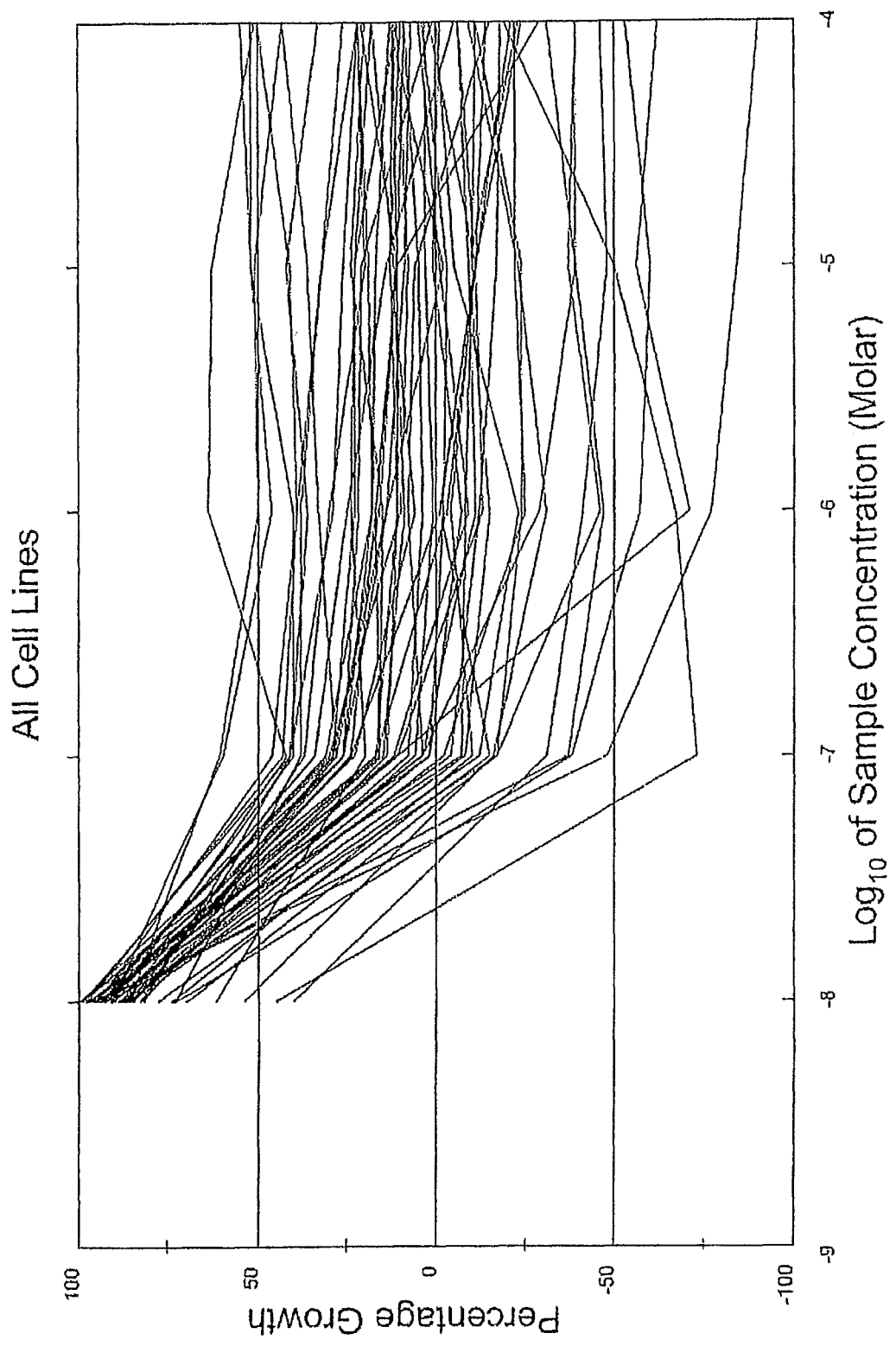
FIG. 7 shows a dose response curve of percentage growth for all of the cell lines shown in FIG. 5.

FIG. 7 shows a dose response curve of percentage growth for all of the cell lines shown in FIG. 5.

Figure 8A:
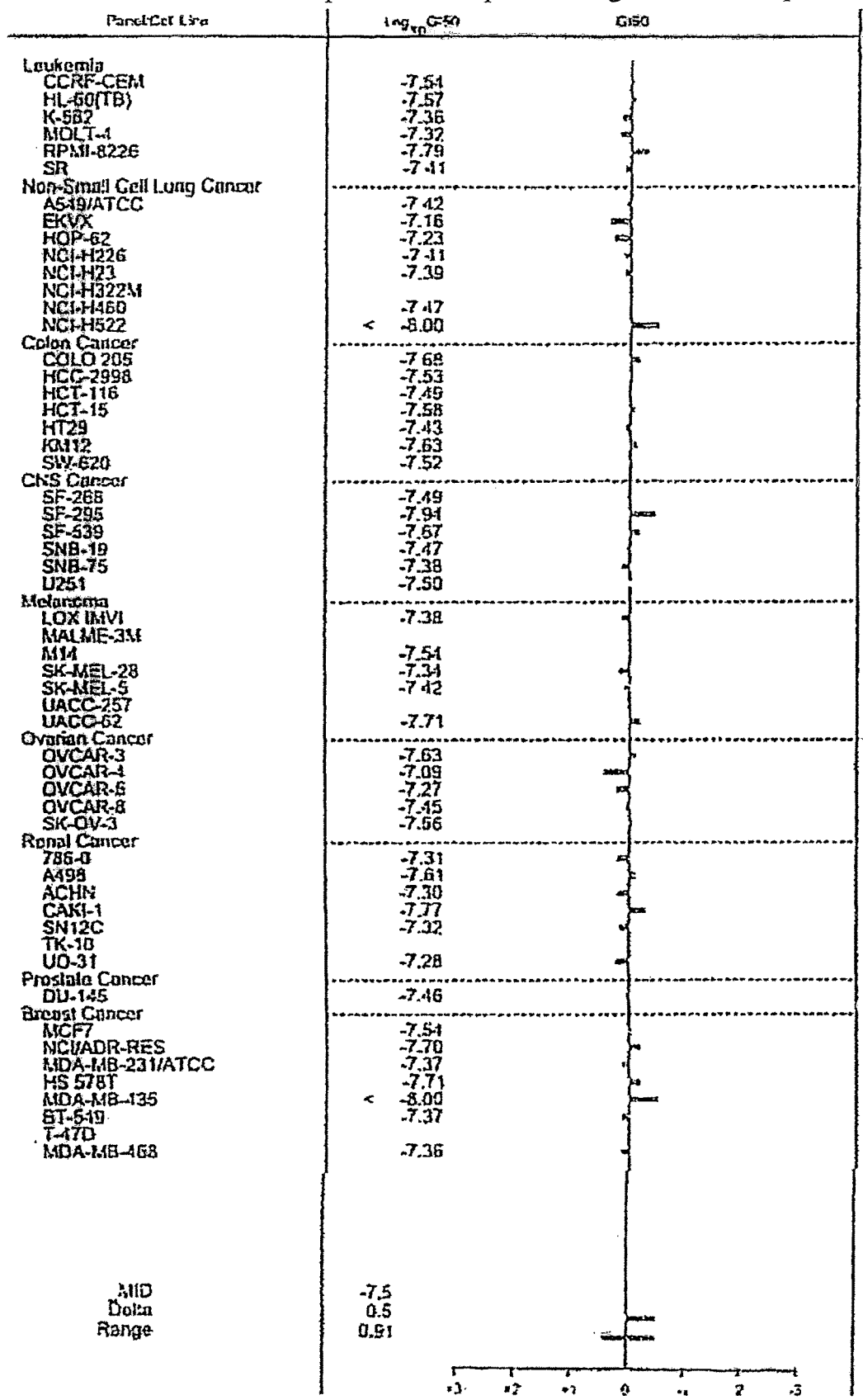
FIG. 8a shows mean graphs for specific cancer types and corresponding cell lines shown in FIG. 5.
Figure 8B:
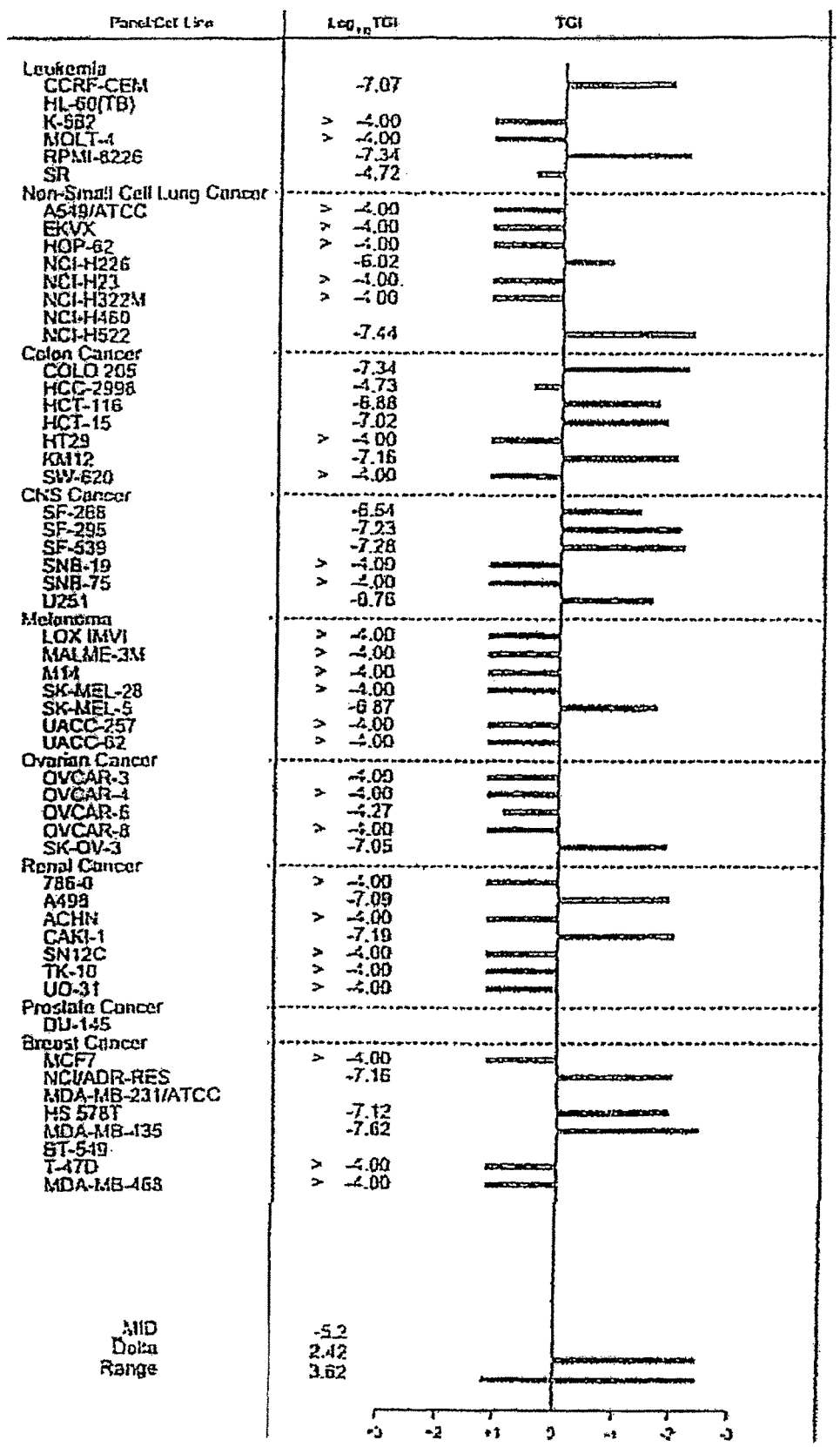
FIG. 8b shows mean graphs for specific cancer types and corresponding cell lines shown in FIG. 5.
Figure 8C:
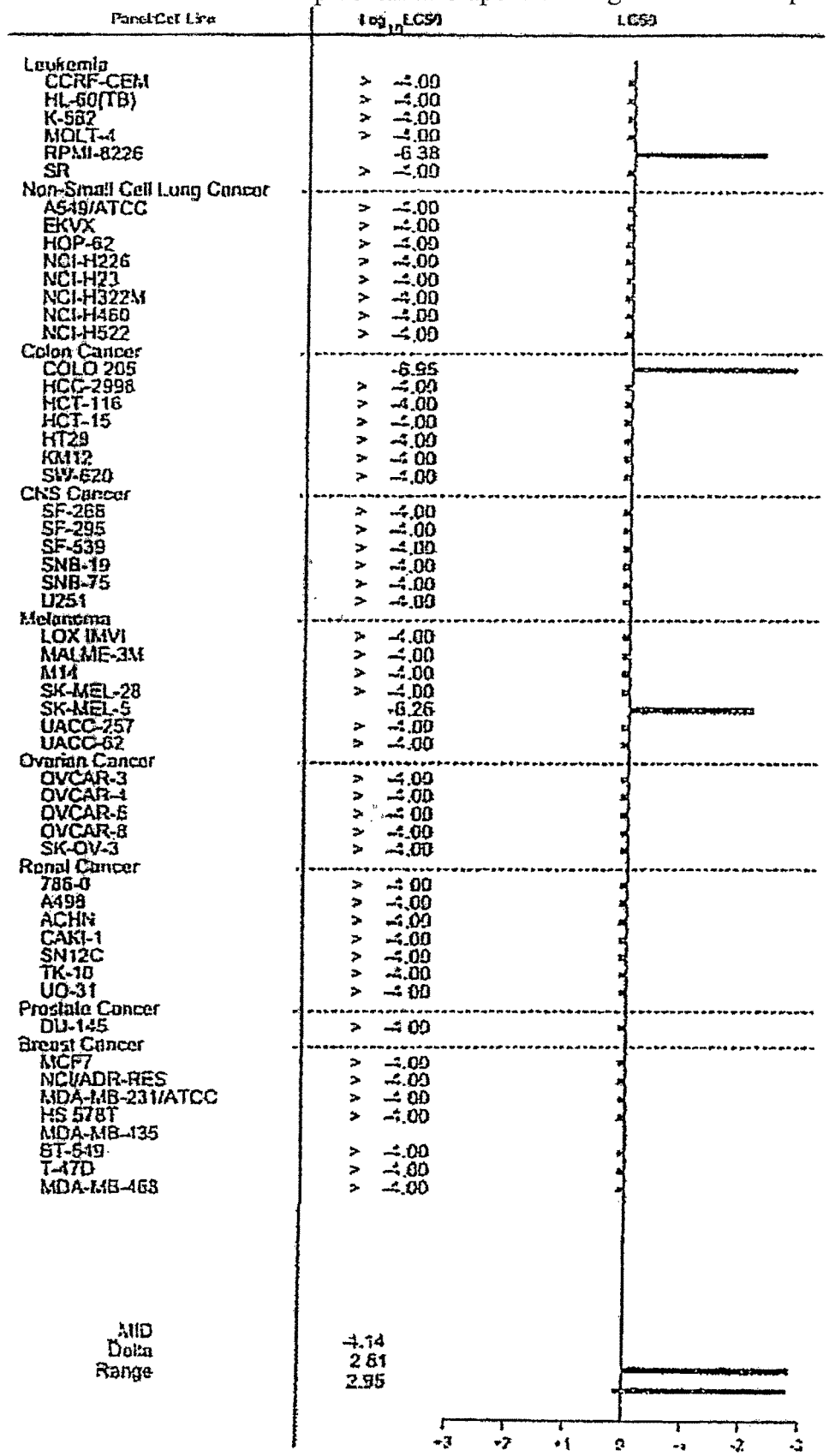
FIG. 8c shows mean graphs for specific cancer types and corresponding cell lines shown in FIG. 5.

FIGS. 8a, 8b, and 8c show mean graphs for specific cancer types and corresponding cell lines shown in FIG. 5.

Synthesis of Tricyclic Compounds

Analytical samples were dried in vacuo (0.2 mm Hg) in a CHEM-DRY drying apparatus over $P_2O_5$ at 80° C. Melting points were determined on a MEL-TEMP II melting point apparatus with FLUKE 51 K/J electronic thermometer and are uncorrected. Nuclear magnetic resonance spectra for proton ($^1$H NMR) were recorded on a Bruker WH-400 (400 MHz) spectrometer. The chemical shift values are expressed in ppm (parts per million) relative to tetramethylsilane as an internal standard: s, singlet; d, doublet; t, triplet; q, quartet; m, multiplet; br, broad singlet. Thin-layer chromatography (TLC) was performed on Whatman Sil G/UV254 silica gel plates with a fluorescent indicator, and the spots were visualized under 254 and 366 nm illumination. Proportions of solvents used for TLC are by volume. Column chromatography was performed on a 230-400 mesh silica gel (Fisher, Somerville, N.J.) column. Elemental analyses were performed by Atlantic Microlab, Inc., Norcross, Ga. Element compositions are within ±0.4% of the calculated values. Fractional moles of water or organic solvents frequently found in some analytical samples could not be prevented in spite of 24-48 h of drying in vacuo and were confirmed where possible by their presence in the $^1$H NMR spectra. All solvents and chemicals were purchased from Aldrich Chemical Co. or Fisher Scientific and were used as received.

Synthesis of AAG3

Analytical samples were dried in vacuo (0.2 mm Hg) in a CHEM-DRY drying apparatus over $P_2O_5$ at 80° C. Melting points were determined on a MEL-TEMP II melting point apparatus with FLUKE 51 K/J electronic thermometer and are uncorrected. Nuclear magnetic resonance spectra for proton ($^1$H NMR) were recorded on a Bruker WH-400 (400 MHz) spectrometer. The chemical shift values are expressed in ppm (parts per million) relative to tetramethylsilane as an internal standard: s, singlet; d, doublet; t, triplet; q, quartet; m, multiplet; br, broad singlet. Thin-layer chromatography (TLC) was performed on Whatman Sil G/UV254 silica gel plates with a fluorescent indicator, and the spots were visualized under 254 and 366 nm illumination. Proportions of solvents used for TLC are by volume. Column chromatography was performed on a 230-400 mesh silica gel (Fisher, Somerville, N.J.) column. Elemental analyses were performed by Atlantic Microlab, Inc., Norcross, Ga. Element compositions are within ±0.4% of the calculated values. Fractional moles of water or organic solvents frequently found in some analytical samples could not be prevented in spite of 24-48 h of drying in vacuo and were confirmed where possible by their presence in the $^1$H NMR spectra. All solvents and chemicals were purchased from Aldrich Chemical Co. or Fisher Scientific and were used as received.

Synthesis of AAG3

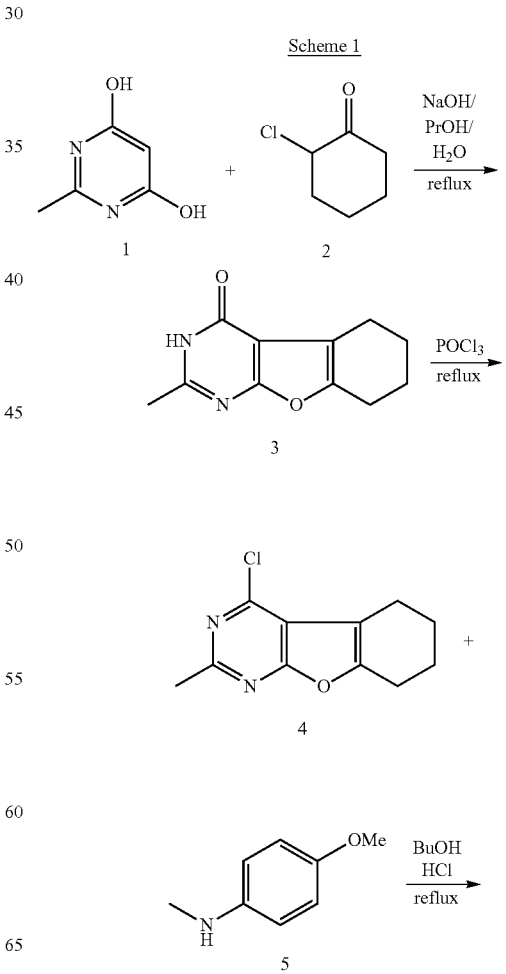

Scheme 1

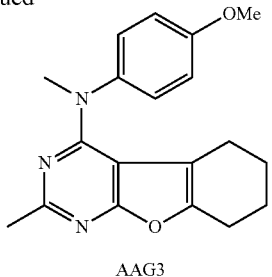

AAG3

Chemistry:

Condensation between dihydroxyl pyrimidine 1 (Scheme 1) and α-Cl-cyclohexanone in basic condition afforded tricyclic furo[2,3-d]pyrimidine 3. Solvent selection was very important for the yield of this reaction. Different solvent including DMF, DMSO, H$_2$O, MeOH/H$_2$O, EtOH/H$_2$O and $^i$PrOH/H$_2$O were tried. Among them $^i$PrOH/H$_2$O as solvent gave the best result. Compound 3 was then treated with POCl$_3$ to afford 4-cholo analogue 4, which reacted with N-methyl aniline 5 and a trace amount of HCl in BuOH to give the target compound AAG3.

Experimental section for Scheme 1:

2-Methyl-5,6,7,8-tetrahydro[1]benzofuro[2,3-d]pyrimidin-4(3H)-one (3). NaOH (0.4 g, 1 mmol) and compound 1 (1.26 g, 1 mmol) were dissolved 10 mL H$_2$O. Compound 2 (1.32 g, 1 mmol) was dissolved in 10 mL $^i$PrOH. After the two solutions were mixed in a 50 mL flask and refluxed for 3 days, the reaction mixture was evaporated to dryness under reduced pressure. The residue was dissolved in a minimum amount of MeOH, and chromatographed on a silica gel column (2 cm×15 cm) with acetyl acetate as the eluent. Fractions that showed the desired single spot at R$_f$=0.55 were pooled and evaporated to dryness to afford 857 mg (42%) of 3 as a white powder: TLC R$_f$ 0.35 (CHCl$_3$/MeOH 6:1); mp>300° C.; $^1$H NMR (DMSO-d$_6$) δ 1.70 (q, 2 H, J=8 Hz), 1.79 (q, 2 H, J=8 Hz), 2.32 (s, 3 H), 2.58 (d, 4 H, J=8 Hz), 12.29 (s, 1 H). Anal. calcd for C$_{11}$H$_{12}$N$_2$O$_2$: C, 64.69; H, 5.92; N, 13.72. Found: C, 64.54; H, 5.97; N, 13.43.

4-Chloro-2-methyl-5,6,7,8-tetrahydro[1]benzofuro[2,3-d]pyrimidine (4). To a 50 mL flask was added 3 (2.04 g, 10 mmol) and 10 mL POCl$_3$. The resulting mixture was refluxed for 2 h, and the solvent was removed under reduced pressure to afford a dark residue. To this was added 30 mL of CHCl$_3$ and 3 g of silica gel. The solvent was evaporated to afford a plug. Column chromatography of the plug with hexane: acetyl acetate=20:1 as eluent afford 1.67 g (82%) of 4 as a yellow solid: TLC R$_f$ 0.41 (Hexane/EtOAc 15:1); mp 42.4-43.8° C.; $^1$H NMR (DMSO-d$_6$) δ 1.79 (q, 2 H, J=8 Hz), 1.87 (q, 2 H, J=8 Hz), 2.63 (s, 3 H), 2.75 (d, 4 H, J=8 Hz).

N-(4-methoxyphenyl)-N,2-dimethyl-5,6,7,8-tetrahydro[1]benzofuro[2,3-d]pyrimidin-4-amine (AAG3). To a 50 mL flask was added 4(111 mg, 0.5 mmol), 5 (77 mg, 0.55 mmol) and 5 mL BuOH. To this solution was added 2 drops of concentrate HCl solution and the mixture was refluxed. TLC indicated the disappearance of starting material 4, the solvent was removed under reduced pressure. To the residue obtained was added silica gel and MeOH and the solvent removed to make a plug. This plug was separated by column chromatography to give 117 g (73%) of AGG3 as white solid; TLC R$_f$ 0.45 (Hexane/EtOAc 3:1); mp 147-149° C.; $^1$H NMR (DMSO-d$_6$) δ 1.19 (s, 3 H), 1.31 (m, 2 H), 1.57 (m, 2 H), 2.57 (s, 3 H), 3.26 (m, 2 H), 3.39 (m, 2 H), 3.75 (s, 3 H), 6.96 (d, 2 H, J=3 Hz), 7.16 (d, 2 H, J=3 Hz) Anal. calcd for: C, 70.57; H, 6.55; N, 12.99. Found. C, 70.63; H, 6.56; N, 12.72.

Synthesis of AAG13

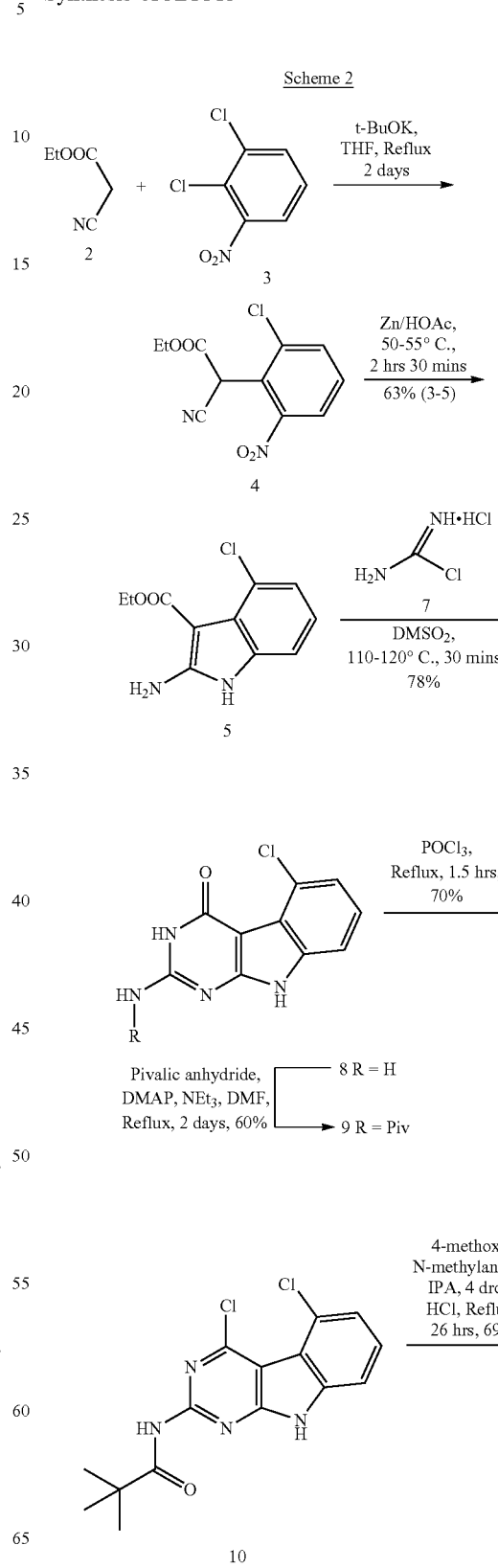

Scheme 2

-continued

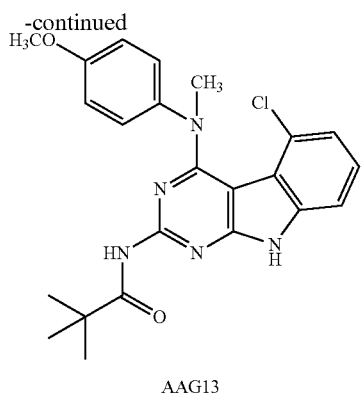

AAG13

Scheme 2a

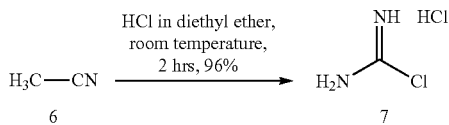

Chemical Discussion

The synthesis of target compounds commenced from commercially available 1,2-dichloro-3-nitro-benzene 3 and ethyl cyanoacetate 2 (Scheme 2). After treating 2 with base potassium tert-butoxide, 3 was added to the reaction mixture. Displacement of the chloro group of 3 by the ethyl cyanoacetate anion provided compound 4 as a viscous yellow liquid. Reduction of the nitro group of 4 followed by cyclization furnished compound 5 as a pink solid. Use of fresh or activated zinc powder is recommended for this reaction. Cyclocondensation of 5 with carbamimidic chloride hydrochloride 6 afforded the tricyclic compound 8 as a brown solid (synthesis of 7 is provided in scheme 2a). Protection of the 2-amino group of 8 using pivalic anhydride under basic conditions provided 9. Compound 10 was prepared by treating 9 with phosphoryl trichloride at reflux. Replacement of the 4-chloro group in 10 with a 4-methoxy-N-methyl aniline group, and simultaneous deprotection of the 2-amino group in 10 was achieved in one step by treating 10 with 4-methoxy-N-methyl aniline in IPA at reflux, in presence of 4 drops of concentrated hydrochloric acid, to obtain the target compound AAG13 in 69% yield.

Experimental Section for Scheme 2 and 2a:

Ethyl(2-chloro-2-nitrophenyl)(cyano)acetate (4). To an ice cold solution of ethylcyanoacetate (10.9 mL, 102.4 mmol) in anhydrous THF (170 mL) under nitrogen, was added potassium tert-butoxide (12.7 g, 107.5 mmol). The formed white suspension was stirred for 15 min, then treated with 2, 3-dichloronitrobenzene (9.83 g, 51.2 mmol). The suspension was heated at reflux for 48 hours. The resulting reddish brown solution was poured in to water, and the aqueous-mixture was acidified to pH 2 with conc. HCl. The mixture was extracted with ether (3×150 mL) and then the combined organic phase was dried (using $Na_2SO_4$) and concentrated to give a dark oil. Flash chromatography using 10:1 hexane:ethyl acetate in a column packed with silica gel, 10 times the weight of the dark oil, provided a viscous yellow liquid 4, which was used without further purification for the next step. TLC R$f$0.23 (hexane-ethyl acetate 3:1). $^1$H NMR δ 1.33-1.38 (t, 3H, $CH_3$); 4.29-4.35 (q, 2H, $CH_2$); 7.59-8.14 (m, 3H, phenyl).

Ethyl-2-amino-4-chloro-1H-indole-3-carboxylate (5). 4 (18 g, 67 mmol) in 250 mL glacial acetic acid, was treated with a single charge of 18 g of zinc dust. The mixture was heated at 55° C. for 45 minutes. Later 6 g more zinc dust was added. After heating for another 105 minutes, the yellow mixture was filtered through a pad of celite. The pad was washed with acetic acid and the filtrate was concentrated to a residue that was distributed between chloroform and water. The organic phase was washed with $NaHCO_3$ (5%) to provide a pink precipitate which was filtered, dried over $P_2O_5$, dissolved in methanol, added silica gel and converted to a silica gel plug by removing the solvent under reduced pressure. The plug was transferred on top of a column packed with silica gel, ten times the weight of plug, eluted with hexane, chloroform, 5% ethylacetate in chloroform and 10% ethylacetate in chloroform. Fractions containing the product 5 (TLC) were pooled and evaporated to give a pink solid. The overall yield from 3 to 5 was 63%. TLC R$f$0.187 (hexane-chloroform 1:1); mp 140-142° C.; $^1$H NMR (DMSO-d6) δ 1.25-1.28 (t, 3H, $CH_3$); 4.18-4.20 (q, 2H, $CH_2$); 6.85 (bs, 2H, 2-$NH_2$, exch); 6.92-7.09 (m, 3H, phenyl); 10.93 (bs, 1H, 9-NH, exch). Anal. Calculated ($C_{11}H_{11}ClN_2O_2$): C, 55.36; H, 4.65; N, 11.74; Cl, 14.85. Found: C, 55.39; H, 4.60; N, 11.65; Cl, 14.96.

Carbamimidic chloride hydrochloride (7). Cyanamide (4.2 g, 0.1 mol) was dissolved in 100 mL of diethyl ether in a 500 mL round bottom flask. The mixture was stirred under nitrogen. 100 mL of 2M HCl in diethyl ether was added to the reaction flask via a 250 mL dropping funnel. Stirring was continued for 2 hours at room temperature. The white salt which precipitated out was filtered and dried. The overall yield for 7 was 96%. Compound 7 was used for the next step without further purification.

2-Amino-5-chloro-3, 9-dihydro-4H-pyrimido[4,5-b]indol-4-one (8). Methyl sulfone (1 g) was heated to melting. Compound 7 (106.22 mg, 1.37 mmol) was added and the resulting mixture was stirred and heated at 110-120° C. to dissolve completely. 5 (200 mg, 0.837 mmol) was added in one part to the reaction mixture. Stirring was continued for 30 minutes. About 10 mL water was added to quench the reaction. Ammonia water was added to neutralize the reaction mixture. Solid precipitated out. This solid was filtered. Obtained solid was dissolved in chloroform and methanol, dried (using $Na_2SO_4$) and recrystallized. The overall yield was 78%. TLC R$f$0.33 (chloroform-methanol 1:1); mp>250° C.; $^1$H NMR (DMSO-d6) δ 6.57 (bs, 2H, 2-$NH_2$ exch); 7.04-7.17 (m, 3H, phenyl); 10.41 (s, 1H, 9-NH, exch); 11.64 (s, 1H, 3-NH, exch). Anal. Calculated ($C_{10}H_7ClN_4O$. 0.3$CH_3OH$): C, 50.65; H, 3.38; N, 22.94; Cl, 14.52. Found: C, 50.91; H, 3.34; N, 22.60; Cl, 14.77.

N-(5-chloro-4-oxo-4,9-dihydro-3H-pyrimido[4,5-b]indol-2-yl)-2,2-dimethyl propanamide (9). Compound 8 (300 mg, 1.27 mmol), 2-dimethyl propanoic anhydride (713.32 mg, 3.83 mmol), dimethyl aminopyridine (7 mg, 0.06 mmol), triethylamine (514.05 mg, 5.08 mmol) were weighed together in a 50 mL round bottom flask. This flask was placed in an oil bath at 60° C. with stirring for 2 days. Then, to the reaction mixture was added 1 g silica gel. The DMF was removed using oil pump and a silica gel plug was made. The plug was transferred on top of a column packed with silica gel, twenty times the weight of plug, eluted with chloroform, 1% methanol in chloroform and 5% methanol in chloroform. Fractions containing the product 9 (TLC) were pooled and evaporated to give solid compound. The overall yield was 40%. TLC R$f$0.45 (chloroform-methanol 10:1), m.p. 185.8-190.1° C., $^1$H NMR: δ 1.27 (s, 9H, pivaloyl;

7.19-7.40 (m, 3H, phenyl); 11.15 (s, 1H, 9-NH, exch); 11.94 (s, 1H, 9-NH, exch); 12.12 (s, 1H, 3-NH, exch).

N-(4,5-dichloro-9H-pyrimido[4,5-b]indol-2-yl)-2,2-dimethyl propanamide (10). To 9 (2 g, 6.274 mmol) was added 30 mL of POCl$_3$ in a 250 mL round bottom flask. The reaction mixture was refluxed at 110-120° C. for 4 hours. After this the POCl$_3$ was evaporated and the mixture was neutralized using NH$_4$OH. The aqueous mixture was filtered (the ppt being the compound). The filtrate too contained some compound. Therefore it was extracted using chloroform and ethyl acetate. The ppt. obtained was dissolved in chloroform and methanol. Both the dissolved ppt. and extracted filtrate were dried using sodium sulfate overnight. To the solution was added silica and solvent was removed under reduced pressure to provide a silica gel plug. The plug was transferred on top of a column packed with silica gel, twenty times the weight of plug, eluted with chloroform, 1% methanol in chloroform and 5% methanol in chloroform. Fractions containing the product 10 (TLC) were pooled and evaporated to give a solid. The overall yield was 70%. TLC R$f$0.86 (chloroform-methanol 5:1), m.p. 245.6-246.1° C., $^1$H NMR: δ 1.24 (s, 9H, pivaloyl); 7.37-7.63 (m, 3H, phenyl); 10.32 (s, 1H, 9-NH, exch); 12.96 (s, 1H, 2-NH, exch). Anal. Calculated (C$_{15}$H$_{14}$Cl$_2$N$_4$O. 0.25 (C$_2$H$_5$)$_2$O): C, 54.02; H, 4.67; N, 15.74. Found: C, 54.14; H, 4.56; N, 15.69.

5-Chloro-N$^4$-(4-methoxyphenyl)-N$^4$-methyl-9H-pyrimido[4,5-b]indole-2,4-diamine AAG13. To 10 (20 mg, 0.06 mmol) was added 4-methoxy-N-methyl aniline (61 mg, 0.44 mmol), 50 mL of Isopropanol, and 4 drops of conc. HCl in a 100 mL round bottom flask. The reaction mixture was refluxed at 110-120° C. for 26 hours, following which the Isopropanol was evaporated and the mixture was basified with ammonia in methanol to obtain a slight precipitate. The resulting precipitate was then dissolved in acetone and methanol. To the solution was added silica, and the solvent was removed under reduced pressure to provide a silica gel plug. The plug was transferred on top of a column packed with silica gel, twenty times the weight of plug, eluted with chloroform and 1% methanol in chloroform. Fractions containing the product AAG13 (TLC) were pooled and evaporated to give a solid which was further purified by washing with hexane. The overall yield was 69%. TLC R$f$0.25 (chloroform-methanol 20:1), m.p. 163-164° C., $^1$H NMR: δ 3.30 (s, 3H, OCH$_3$), 3.66 (s, 3H, N—CH$_3$), 6.55 (s, 2H, NH$_2$, exch), 6.76-7.25 (m, 7H, ArH), 11.65 (s, 1H, 9-NH, exch). Anal. Calculated (C$_{18}$H$_{16}$ClN$_5$O. 0.2 CH$_3$(CH$_2$)$_4$CH$_3$): C, 62.15; H, 5.10; N, 18.87; Cl, 9.55. Found: C, 61.79; H, 4.95; N, 18.72; Cl, 9.48.

Synthesis of AAG101

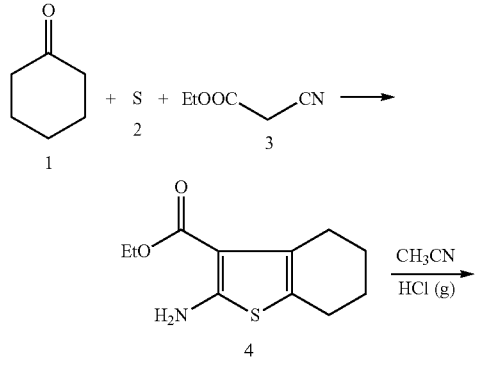

Scheme 3

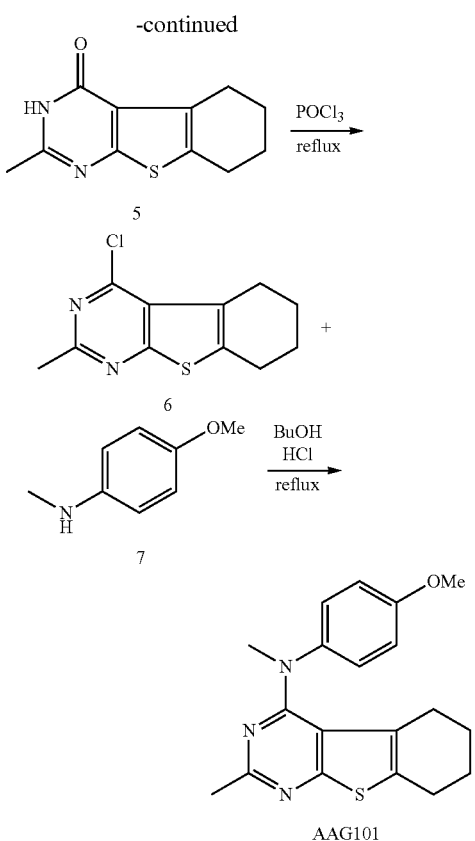

Chemistry:

The Gewald reaction of 1, 2 and 3 afforded bicyclic 4 (Scheme 3). Condensation of 4 and CH$_3$CN under acidic conditions afforded 5, which was converted to the 4-chloro analogue 6 by treating with POCl$_3$. The 4-chloro compound 6 reacted with N-methyl aniline 7 and a trace amount of HCl in BuOH to give compound AAG101. Condensation between 4 and 9 afforded tricyclic compound 10, which was converted to 4-chloro analogue 11 by treating with POCl$_3$. The 4-chloro compound 11 reacted with N-methyl aniline 7 and a trace amount of HCl in BuOH to give compound 12.

Experimental Section for Scheme 3

Ethyl 2-amino-4,5,6,7-tetrahydro-1-benzothiophene-3-carboxylate (4). A mixture of 1 (98 mg, 1 mmol), 2 (32 mg, 1 mmol), 3 (113 mg, 1 mmol) and EtOH (5 mL) was treated dropwise with morpholine (86 mg, 1 mmol) at 45° C. over 15 min. The mixture was stirred for 5 h at 45° C. and 24 h at room temperature. Unreacted sulfur was removed by filtration, and the filtration was concentrated under reduced pressure to afford an orange oil. The residue was loaded on a column packed with silica gel and washed with 10% ethyl acetate in hexane. The fractions containing the desired product (TLC) were pooled and evaporated to afford 184 mg (82%) of 4 as a white solid:

2-Methyl-5,6,7,8-tetrahydro [1]benzothieno[2,3-d]pyrimidin-4(3H)-one (5). To a 25 ml flask was added 4 (225 mg, 1 mmol) and 10 ml CH$_3$CN. HCl gas was passed through the solution for 3 h, before the solvent was evaporated under reduced pressure. The residue was dissolved in 10 mL distilled water and treated with ammonia water solution to generate a white precipitate. The precipitate was collected by filtration to afford 143 mg (62%) of 5 as a white solid: $^1$H NMR (DMSO-d$_6$) δ 1.75 (m, 4 H), 2.48 (s, 3 H), 2.69 (m, 2 H), 2.83 (m, 2 H), 12.16 (s, 1 H). Anal. ($C_{11}H_{12}N_2OS$) m/z (ESI) 220.067811 $[M]^+$.

4-Chloro-2-methyl-5,6,7,8-tetrahydro[1]benzothieno[2,3-d]pyrimidine (6). To a 50 mL flask was added 5 (220 mg, 1 mmol) and 5 mL $POCl_3$. The resulting mixture was refluxed for 2 h, and the solvent was removed under reduced pressure to afford a dark residue. To this was added 30 mL of $CHCl_3$ and 300 mg of silica gel. The solvent was evaporated to afford a plug. Column chromatography of the plug with hexane: acetyl acetate=20:1 as eluent afford 192 g (81%) of 6 as a yellow solid: $^1$H NMR (DMSO-$d_6$) δ 1.82 (m, 4 H), 2.63 (s, 3 H), 2.84 (m, 2 H), 2.96 (m, 2 H).

N-(4-methoxyphenyl)-N,2-dimethyl-5,6,7,8-tetrahydro[1]benzothieno[2,3-d]pyrimidin-4-amine (AAG101). To a 50 mL flask was added 6 (119 mg, 0.5 mmol), 7 (77 mg, 0.55 mmol) and 5 mL BuOH. To this solution was added 2 drops of concentrate HCl solution and the mixture was refluxed. TLC indicated the disappearance of starting material 6, the solvent was removed under reduced pressure. To the residue obtained was added silica gel and MeOH and the solvent removed to make a plug. This plug was separated by column chromatography to give 110 g (65%) of 8 as a white powder: mp 108-109° C.; $R_f$ 0.36 (Hexane/EtOAC 3:1); $^1$H NMR (DMSO-$d_6$) δ 2.14 (s, 3 H), 2.45 (s, 3 H), 3.43 (s, 3 H), 3.81 (s, 3 H), 4.55 (s, 1 H), 7.04 (d, 2 H, J=2.8 Hz), 7.25 (d, 2 H, J=2.8 Hz). Anal. ($C_{19}H_{21}N_3OS$) m/z (ESI) 340.1484 $[M]^+$.

Synthesis of AAG102

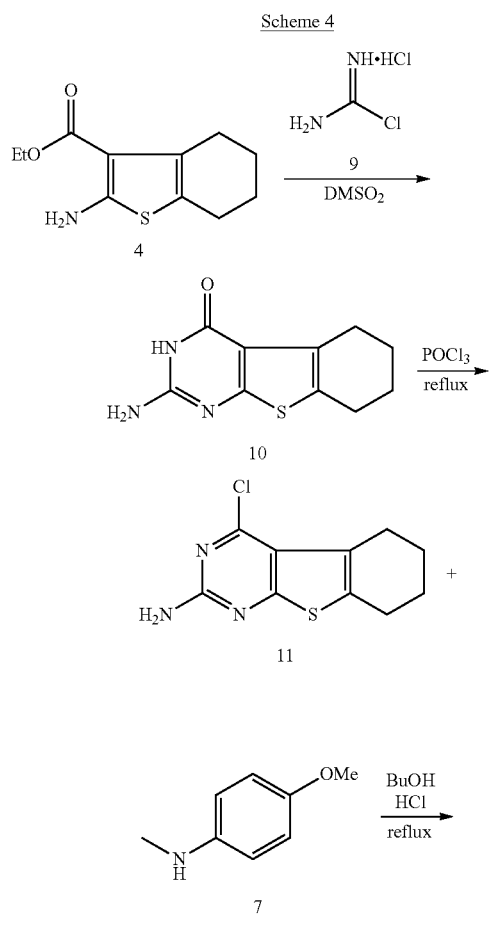

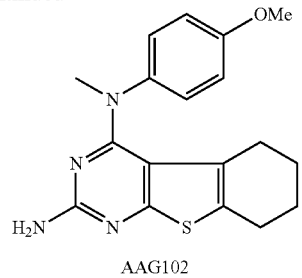

AAG102

Chemistry:

The Gewald reaction of 1, 2 and 3 afforded bicyclic 4 (Scheme 3). Condensation of 4 and 9 afforded 10, which was converted to the 4-chloro analogue 11 by treating with $POCl_3$. The 4-chloro compound 11 reacted with N-methyl aniline 7 and a trace amount of HCl in BuOH to give compound AAG102.

Experimental Section for Scheme 4

2-amino-5,6,7,8-tetrahydro[1]benzothieno[2,3-d]pyrimidin-4(3H)-one (10). To a 50 mL flask was added 4 (225 mg, 1 mmol), 9 (452 mg, 4 mmol) in $DMSO_2$ (500 mg) was heated at 150° C. for 2 h. The mixture was cooled to room temperature. 15 mL water was added and ammonium hydroxide was used to neutralize the suspension. The brown solid was obtained by filtration. Washed with water and dried. The solid was dissolved in methanol and silica gel was added. A dry silica gel plug obtained after evaporation. The plug was then loaded on the column and washed with 5% methanol in chloroform. The fractions containing the desired product (TLC) were pooled and evaporated to afford 132 mg (60%) of 10 as a white solid: $^1$H NMR (DMSO-$d_6$) δ 1.71 (m, 4 H), 2.60 (m, 2 H), 2.72 (m, 2 H), 6.38 (s, 2 H), 10.72 (s, 1 H). Anal. calcd for $C_{10}H_{11}N_3OS$: C, 54.28; H, 5.01; N, 18.99; 0, 7.23; S, 14.49. Found: C, 53.45; H, 5.06; N, 18.26; S, 14.02.

4-Chloro-5,6,7,8-tetrahydro[1]benzothieno[2,3-d]pyrimidin-2-amine (11). To a 50 mL flask was added 10 (221 mg, 1 mmol) and 10 mL $POCl_3$. The resulting mixture was refluxed for 2 h, and the solvent was removed under reduced pressure to afford a dark residue. To this was added 30 mL of $CHCl_3$ and 300 mg of silica gel. The solvent was evaporated to afford a plug. Column chromatography of the plug with hexane: acetyl acetate=20:1 as eluent afford 105 mg (44%) of 11 as a yellow solid:

$N^4$-(4-methoxyphenyl)-$N^4$-methyl-5,6,7,8-tetrahydro[1]benzothieno[2,3-d]pyrimidine-2,4-diamine (AAG102). To a 50 mL flask was added 11 (119 mg, 0.5 mmol), 7 (77 mg, 0.55 mmol) and 5 mL BuOH. To this solution was added 2 drops of concentrate HCl solution and the mixture was refluxed. TLC indicated the disappearance of starting material 11, the solvent was removed under reduced pressure. To the residue obtained was added silica gel and MeOH and the solvent removed to make a plug. This plug was separated by column chromatography to give 105 mg (62%) of 12 as a white powder: $^1$H NMR (DMSO-$d_6$) δ 1.38 (m, 2 H), 1.52 (m, 2 H), 1.68 (m, 2 H), 2.07 (m, 2 H), 3.69 (s, 3 H), 6.37 (s, 2 H), 6.84 (m, 4 H). Anal. ($C_{18}H_{20}N_4OS$) m/z (ESI) 341.1436 $[M+1]^+$

Scheme 5

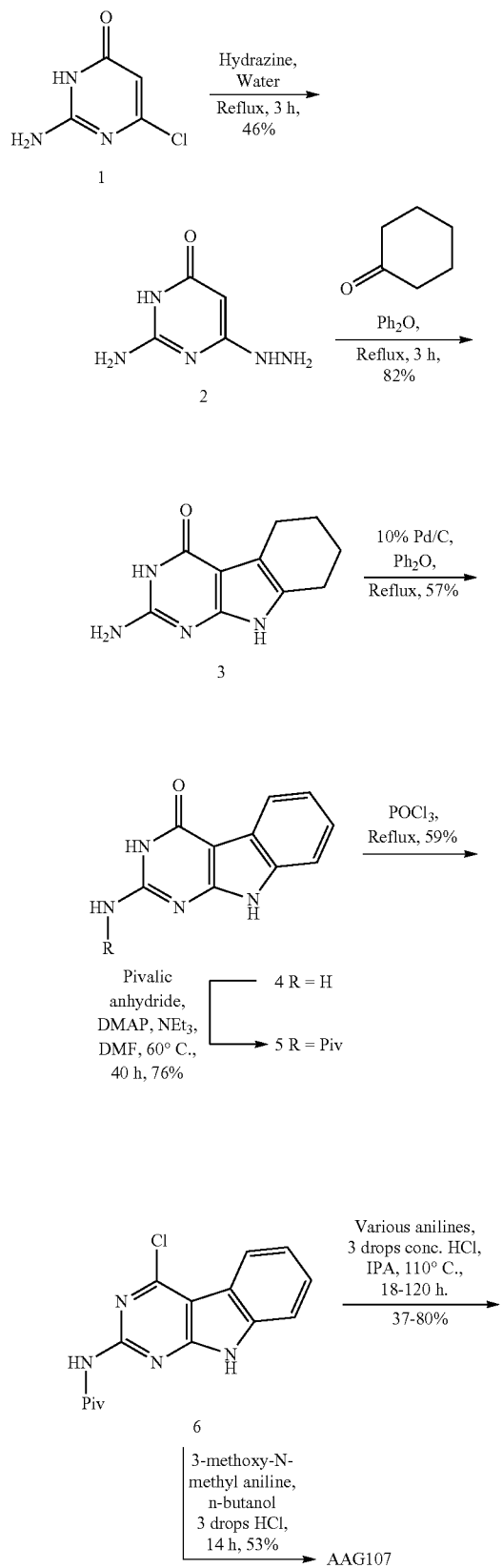

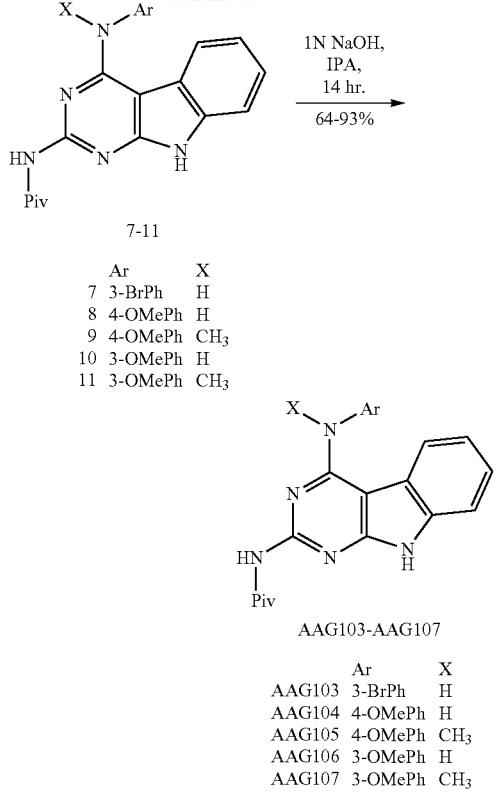

| | Ar | X |
|---|---|---|
| 7 | 3-BrPh | H |
| 8 | 4-OMePh | H |
| 9 | 4-OMePh | CH$_3$ |
| 10 | 3-OMePh | H |
| 11 | 3-OMePh | CH$_3$ |

AAG103-AAG107

| | Ar | X |
|---|---|---|
| AAG103 | 3-BrPh | H |
| AAG104 | 4-OMePh | H |
| AAG105 | 4-OMePh | CH$_3$ |
| AAG106 | 3-OMePh | H |
| AAG107 | 3-OMePh | CH$_3$ |

Chemical Discussion:

The synthesis of target compounds commenced from commercially available 2-amino-6-chloropyrimidin-4(3H)-one (1) using a method reported by Taylor et al.[1] to obtain 2 in 46% yield (Scheme 5). A thermal Fisher Indole-cyclization of 2 and cyclohexanone in diphenyl ether furnished the tricyclic scaffold 3. The partially saturated ring in 3 was oxidized using 10% Pd/C to provide 4 in 57% yield. Pivaloyl protection of 4 gave 5, and subsequent chlorination afforded the synthetic intermediate 6. Compound 6 was treated with various substituted anilines in isopropanal and three drops of concentrated HCl at reflux to provide the penultimate compounds 7-11 in yields of 37 to 80%. The pivaloyl group in 7-11 was removed by a basic hydrolysis of the 2-amide linkage in these compounds using 1N NaOH to give the desired target compounds-AAG103-AAG107 in yields ranging from 64-93%. AAG107 was also synthesized by treating 6 with 3-methoxy-N-methyl aniline, in n-butanol and three drops of conc. HCl at reflux, to afford 16 in a yield of 53%

Experimental Section for Scheme 5:

2-Amino-6-hydrazinopyrimidin-4(3H)-one (2). A stirred suspension of 15.0 g (103 mmol) of 1 in 250 mL water was added 12 g (375 mmol) of anhydrous hydrazine, and the mixture was heated at reflux for 3 h. The resulting clear solution was cooled, and the precipitate which separated was collected by filtration, washed with water followed by ethanol and dried to give 6.6 g (46%) of white solid. mp decomposes at 313° C. (Literature mp 314-315° C., see Taylor, E. C.; Cocuzza, J. A. Synthesis and Properties of 7-Azaxanthopterin. J. Org. Chem. 1979, 44, 1125-1128).

2-Amino-3,5,6,7,8,9-hexahydro-4H-pyrimido[4,5-b]indol-4-one (3). A mixture of 2 (350 mg, 2.5 mmol) and cyclohexanone (245 mg, 2.5 mmol) was stirred and heated at 120-130° C. in an oil bath overnight and then under reflux at 250° C. for 3 hours. After cooling to room temperature, hexane (50 mL) was added and the precipitated solid was collected by filtration. The solid was dried over $P_2O_5$, dissolved in methanol and added silica (three times the weight of solid), following which the solvent was removed under reduced pressure to obtain a dry plug. The plug was loaded on top of a column packed with chloroform. The weight of silica in the column was thirty times the weight of the plug. Flash chromatography using 20% methanol in chloroform afforded 82% of yellow solid. TLC $R_f$ 0.35 (chloroform-methanol 5:1); mp decomposes at 338° C.; $^1$H NMR (DMSO-d$^6$) δ 1.64-1.69 (m, 4 H, 6-CH$_2$, 7—CH$_2$), 2.42 (m, 2 H, 5-CH$_2$), 2.53 (m, 2 H, 8-CH$_2$), 5.88 (s, 2 H, 2-NH$_2$, exch), 10.02 (s, 1 H, 3-NH, exch), 10.50 (s, 1 H, 9-NH, exch). Anal. Calculated ($C_{10}H_{12}N_4O$. 0.4 $H_2O$): C, 56.80; H, 6.10; N, 26.49. Found: C, 56.90; H, 6.06; N, 26.49.

2-Amino-3,9-dihydro-4H-pyrimido[4,5-b]indol-4-one (4). A mixture of 3 (50 mg, 0.24) and 10% Pd/C (24 mg) in Ph$_2$O (5 mL) was heated to 250° C. for 3 hours. The reaction mixture was cooled to room temperature and DMF (20 mL) was added to dissolve the product. The catalyst was filtered off through celite and washed with DMF to give a solution which was evaporated to give solid residue. Hexane (25 mL) was added to the residue and the solid was filtered. The solid was dissolved in DMF (5 mL) and silica gel (1 g) was added. Solvent was removed under reduced pressure to afford plug, which was loaded on top of a silica gel column packed with chloroform, having silica, thirty times by weight of the plug, and eluted with 20% methanol in chloroform to afford 28 mg of 4 as a pale white solid in 57% yield. TLC $R_f$ 0.32 (chloroform-methanol 5:1); mp>340° C.; $^1$H NMR (DMSO-d$^6$) δ 6.51 (s, 2 H, NH$_2$), 7.04 (m, 2 H, Ar—H), 7.24 (m, 1 H, Ar—H), 7.7 (m, 1 H, Ar—H), 10.47 (s, 1 H, 3-NH, exch), 11.35 (s, 1 H, 9-NH, exch).

2,2-Dimethyl-N-(4-oxo-4,9-dihydro-3H-pyrimido[4,5-b]indol-2-yl)propanamide (5). Compound 4 (50 mg, 0.25 mmol), trimethyl acetic anhydride (6 g, 32 mmol), DMAP (16 mg, 0.13 mmol), and triethylamine (101 mg, 1 mmol) were dissolved in 8 mL of DMF. The mixture was heated at 60° C. for 40 hours. The DMF and trimethyl acetic anhydride were removed under reduced pressure using oil pump. The residue thus obtained was dissolved in methanol, and was added 3 g of silica gel. The solvent was removed under reduced pressure to afford a dry plug. The plug was loaded on top of a silica gel column packed with chloroform, having silica, twenty times by weight of the plug, and eluted with 1% methanol in chloroform to obtain 52 mg of 5 as a yellow solid in 73% yield. TLC $R_f$ 0.67 (chloroform-methanol 5:1); mp decomposes at 322° C.; $^1$H NMR (DMSO-d$^6$) δ 1.30 (s, 9 H, C(CH$_3$)$_3$), 7.17-7.94 (m, 4 H, Ar—H), 11.12 (s, 1 H, NH, exch), 11.85 (s, 1 H, NH, exch), 12.01 (s, 1 H, NH, exch). Anal. Calculated ($C_{15}H_{16}N_4O_2$. 0.3 $H_2O$): C, 62.18; H, 5.77; N, 19.33. Found: C, 62.24; H, 5.83; N, 18.98.

N-(4-chloro-9H-pyrimido[4,5-b]indol-2-yl)-2,2-dimethylpropanamide (6). In a 50 mL R.B.F. was placed 5 (56 mg, 0.17 mmol) and phosphoryl trichloride (15 mL). The mixture was stirred and heated at reflux for 4 hours. The phosphoryl trichloride was evaporated under reduced pressure using a vacuum aspirator. The resulting residue was cooled in an ice and water mixture, and neutralized with ammonium hydroxide solution to yield a precipitate that was filtered and dried over $P_2O_5$. The filtrate was extracted with chloroform and dried over sodium sulfate. The dry precipitate and filtrate were combined and evaporated to provide 35 mg of 6 as a brown solid in 59% yield. Compound 6 was used without further purification for the subsequent step. TLC $R_f$ 0.65 (chloroform-methanol 10:1); mp 234° C.; $^1$H NMR (DMSO-d$^6$) δ 1.24 (s, 9 H, C(CH$_3$)$_3$), 7.36-8.17 (m, 4 H, Ar—H), 10.25 (s, 1 H, 2-NH, exch), 12.55 (s, 1 H, 9-NH, exch). Anal. Calculated ($C_{15}H_{15}ClN_4O$. 0.15 $H_2O$): C, 58.98; H, 5.04; N, 18.34; Cl, 11.60. Found: C, 59.00; H, 5.09; N, 17.97; Cl, 11.83.

General procedure for the synthesis of N-{4-[substituted phenyl amino]-9H-pyrimido[4,5-b]indol-2-yl}-2,2-dimethylpropanamides 7-11. Compound 6 (1 equivalent) was dissolved in isopropanol, and to this solution was added a substituted aniline (7.5 equivalents). Three drops of conc. HCl were added, and the resulting mixture was stirred and heated at 110° C. from 1 to 5 days, depending upon the aniline used. For work up of this reaction, the solvent was removed under reduced pressure, the mixture was basified with ammonia in methanol, dissolved in methanol, added silica, and the solvent was evaporated to give a dry plug. The plug was loaded on top of a silica gel column packed with chloroform and having silica, fifty times by weight of the plug, and eluted with 0.2% methanol in chloroform to obtain compounds 7-11 in yields of 37-80%.

N-{4-[(3-bromophenyl)amino]-9H-pyrimido[4,5-b]indol-2-yl}-2,2-dimethylpropanamide (7). Using the general procedure described above, the reaction of 6 (181 mg, 0.59 mmol) and 3-bromoaniline (771 mg, 4.48 mmol), was run for 26 hours, to provide 209 mg of 7 as a white solid in 80% yield. TLC $R_f$ 0.28 (chloroform-methanol 20:1); mp 286.7-287.5° C.; $^1$H NMR (DMSO-d$^6$) δ 1.27 (s, 9 H, C(CH$_3$)$_3$), 7.19-7.49 (m, 4 H, Ar—H), 8.18-8.46 (m, 4 H, Ar—H), 8.79 (s, 1 H, 4-NH, exch), 9.64 (s, 1 H, 2-NH, exch), 11.89 (s, 1 H, 9-NH, exch). Anal. Calculated ($C_{21}H_{20}BrN_5O$): C, 57.54; H, 4.59; N, 15.97; Br, 18.22. Found: C, 57.34; H, 4.65; N, 15.80; Br, 17.96.

N-{4-[(3-methoxyphenyl)amino]-9H-pyrimido[4,5-b]indol-2-yl}-2,2-dimethylpropanamide (8). Using the general procedure described above, the reaction of 6 (80 mg, 0.26 mmol) and 4-methoxyaniline (244 mg, 1.98 mmol) was run for 18 hours, to provide 52 mg of 8 as a white solid in 51% yield. TLC $R_f$ 0.55 (chloroform-methanol 15:1); mp 266.8-267° C.; $^1$H NMR (DMSO-d$^6$) δ 1.23 (s, 9 H, C(CH$_3$)$_3$), 3.75 (s, 3 H, OCH$_3$), 6.88-8.26 (m, 8 H, Ar—H), 8.55 (s, 1 H, 4-NH, exch), 9.41 (s, 1 H, 2-NH, exch), 11.79 (s, 1 H, 9-NH, exch). Anal. Calculated ($C_{22}H_{23}N_5O_2$. 0.4 $H_2O$): C, 66.61; H, 6.04; N, 17.65. Found: C, 66.61; H, 6.00; N, 17.37.

N-{4-[(3-methoxyphenyl)(methyl)amino]-9H-pyrimido[4,5-b]indol-2-yl}-2,2-dimethylpropanamide (9). Using the general procedure described above, the reaction of 6 (180 mg, 0.59 mmol) and 4-methoxy-N-methylaniline (612 mg, 4.46 mmol) was run for 72 hours, to provide 109 mg of 9 as brown crystals in 45% yield. TLC $R_f$ 0.62 (chloroform-methanol 15:1); mp 248.2-249° C.; $^1$H NMR (DMSO-d$^6$) δ 1.26 (s, 9 H, C(CH$_3$)$_3$), 3.61 (s, 3 H, OCH$_3$), 3.74 (s, 3 H, NCH$_3$), 5.76-7.29 (m, 8H, Ar—H), 9.49 (s, 1 H, 2-NH, exch), 11.81 (s, 1 H, 9-NH, exch). Anal. Calculated ($C_{23}H_{25}N_5O_2$. 0.55 $CH_3OH$): C, 67.16; H, 6.51; N, 16.63. Found: C, 67.33; H, 6.49; N, 16.28.

N-{4-[(4-methoxyphenyl)amino]-9H-pyrimido[4,5-b]indol-2-yl}-2,2-dimethylpropanamide (10). Using the general procedure described above, the reaction of 6 (160 mg, 0.52 mmol) and 3-methoxyaniline (488 mg, 3.96 mmol) was run for 36 hours, to provide 107 mg of 10 as an off white solid in 52% yield. TLC $R_f$ 0.64 (chloroform-methanol 15:1); mp 219.4-220.2° C.; $^1$H NMR (DMSO-d$^6$) δ 1.23 (s, 9 H, C(CH$_3$)$_3$), 3.8 (s, 3 H, OCH$_3$), 6.57-8.31 (m, 8 H, Ar—H), 8.62 (s, 1 H, 4-NH, exch), 9.59 (s, 1 H, 2-NH, exch), 11.85

(s, 1 H, 9-NH, exch). Anal. Calculated ($C_{23}H_{25}N_5O_2$. 0.55 $CH_3OH$): C, 67.16; H, 6.51; N, 16.63. Found: C, 67.33; H, 6.49; N, 16.28.

N-{4-[(4-methoxyphenyl)(methyl)amino]-9H-pyrimido[4,5-b]indol-2-yl}-2,2-dimethylpropanamide (11). Using the general procedure described above, the reaction of 6 (180 mg, 0.59 mmol) and 4-methoxy-N-methylaniline (612 mg, 4.46 mmol) was run for 120 hours, to provide 88 mg of 11 as a brown solid in 37% yield. TLC $R_f$ 0.57 (chloroform-methanol 15:1); mp 288.5-289.4° C.; $^1H$ NMR (DMSO-$d^6$) δ 1.26 (s, 9 H, $C(CH_3)_3$,) 3.60 (s, 3 H, $OCH_3$), 3.69 (s, 3 H, $NCH_3$), 5.87-7.33 (m, 8 H, Ar—H), 9.58 (s, 1 H, 2-NH, exch), 11.88 (s, 1 H, 9-NH, exch).

General procedure for the synthesis of $N^4$-substituted-9H-pyrimido[4,5-b]indole-2,4-diamine AAG103-AAG107. Compounds 7-11 were dissolved individually in isopropanol. About 4 mL of 1 N NaOH was added to this solution and the resulting mixture was stirred and heated at 110° C. from 14 hours. For work up of this reaction, the solvent was removed under reduced pressure, and the residue was dried over $P_2O_5$. The dry residue was dissolved in methanol, added silica, and the solvent was evaporated to give a dry plug. The plug was loaded on top of a silica gel column (having silica, fifteen times by weight of the plug and packed with chloroform), and eluted with 1% methanol in chloroform to obtain compounds AAG103-AAG107 respectively. These compounds were washed with nonpolar solvents (hexane, diethyl ether) before being sent for elemental analysis. The yields ranged from 64-93%.

$N^4$-(3-bromophenyl)-9H-pyrimido[4,5-b]indole-2,4-diamine AAG103. Using the general procedure described above, the reaction of 7 (209 mg, 0.47 mmol) and 1 N NaOH provided 128 mg of AAG103 as a white solid in 76% yield. TLC $R_f$ 0.36 (chloroform-methanol 15:1); mp 233.6° C.; $^1H$ NMR (DMSO-$d^6$) δ 6.26 (s, 2 H, $NH_2$, exch), 7.09-8.09 (m, 8 H, Ar—H), 8.44 (s, 1 H, 4-NH, exch), 11.32 (s, 1 H, 9-NH, exch). Anal. Calculated ($C_{16}H_{12}BrN_5$): C, 54.25; H, 3.41; N, 19.77; Br, 22.55. Found: C, 54.38; H, 3.48; N, 19.56; Br, 22.29.

$N^4$-(3-methoxyphenyl)-9H-pyrimido[4,5-b]indole-2,4-diamine AAG104. Using the general procedure described above, the reaction of 8 (90 mg, 0.23 mmol) and 1 N NaOH provided 65 mg of AAG104 as a transparent solid in 92% yield. TLC $R_f$ 0.34 (chloroform-methanol 15:1); mp 225.2-225.6° C.; $^1H$ NMR (DMSO-$d^6$) δ 3.74 (s, 3 H, $OCH_3$), 6.05 (s, 2 H, $NH_2$, exch), 6.88-8.07 (m, 8 H, Ar—H), 8.16 (s, 1 H, 4-NH, exch), 11.20 (s, 1 H, 9-NH, exch). Anal. Calculated ($C_{17}H_{15}N_5O$. 0.15 $(C_2H_5)_2O$): C, 66.79; H, 5.25; N, 22.13. Found: C, 66.77; H, 5.08; N, 22.13.

$N^4$-(3-methoxyphenyl)-$N^4$-methyl-9H-pyrimido[4,5-b]indole-2,4-diamine AAG105. Using the general procedure described above, the reaction of 9 (90 mg, 0.22 mmol) and 1 N NaOH provided 66 mg of AAG105 as a white solid in 93% yield. TLC $R_f$ 0.27 (chloroform-methanol 15:1); mp 245.3-245.7° C.; $^1H$ NMR (DMSO-$d^6$) δ 3.48 (s, 3 H, $OCH_3$), 3.71 (s, 3 H, $NCH_3$), 6.20 (s, 2 H, $NH_2$, exch), 5.75-7.15 (m, 8 H, Ar—H), 11.22 (s, 1 H, 9-NH, exch). Anal. Calculated ($C_{18}H_{17}N_5O$. 0.17 $H_2O$): C, 67.05; H, 5.42; N, 21.72. Found: C, 67.06; H, 5.37; N, 21.56.

$N^4$-(4-methoxyphenyl)-9H-pyrimido[4,5-b]indole-2,4-diamine AAG106. Using the general procedure described above, the reaction of 10 (80 mg, 0.20 mmol) and 1 N NaOH provided 40 mg of AAG106 as an off-white solid in 64% yield. TLC $R_f$ 0.30 (chloroform-methanol 15:1); mp 208.9-209.1° C.; $^1H$ NMR (DMSO-d6) δ 3.76 (s, 3 H, $OCH_3$), 6.19 (s, 2 H, $NH_2$, exch), 7.09-8.05 (m, 8 H, Ar—H), 8.26 (s, 1 H, 4-NH, exch), 11.27 (s, 1 H, 9-NH, exch). Anal. Calculated ($C_{17}H_{15}N_5O$. 0.35 $CH_3OH$): C, 65.83; H, 5.22; N, 22.12. Found: C, 66.08; H, 5.22; N, 21.81.

$N^4$-(4-methoxyphenyl)-$N^4$-methyl-9H-pyrimido[4,5-b]indole-2,4-diamine AAG107. Using the general procedure described above, the reaction of 11 (100 mg, 0.24 mmol) and 1 N NaOH provided 58 mg of AAG107 as a white solid in 73% yield. Alternatively, AAG107 can also be synthesized by treating 6 (90 mg, 0.3 mmol) with 3-methoxy-N-methylaniline (306 mg, 2.23 mmol) in presence of 3 drops HCl and solvent n-butanol under reflux conditions for 14 hours. The yield from 6 to AAG107 using this method is 53%. TLC $R_f$ 0.34 (chloroform-methanol 15:1); mp 233.6° C.; $^1H$ NMR (DMSO-$d^6$) δ 3.55 (s, 3 H, $OCH_3$), 3.58 (s, 3 H, $NCH_3$), 6.19 (s, 2 H, $NH_2$, exch), 5.87-7.18 (m, 8 H, Ar—H), 11.27 (s, 1 H, 9-NH, exch).

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of treating a patient diagnosed with cancer comprising administering to the patient a therapeutically effective amount of a compound of Formula I, or a pharmaceutically acceptable salt of the compound of Formula I:

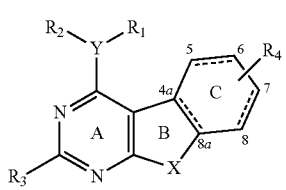

wherein both B and C rings may be completely or partially saturated with respect to bonds 4a-8a, 5-6 and 7-8; the C ring may have an $R_4$ attached to the C ring at positions 5, 6, 7 or 8, or a combination of one or more of these positions depending on the saturation level of the C ring and wherein $R_4$ may be the same or different when attached to a plurality of the 5, 6, 7, or 8 positions of the C ring;

$R_1$ and $R_2$ each independently is one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

$R_1$ and $R_2$ are the same or different with the exception that $R_1$ and $R_2$ may not each be hydrogen at the same time;

$R_3$ is one of (a) a hydrogen (H), (b) an alkyl having from one to ten carbon atoms and having a straight or a branched configuration, and wherein the alkyl is partially or completely saturated; (c) an $NH_2$, (d) an $NHR_7$, (e) an $NR_7R_8$, (f) an OH, (g) an OR, (h) an SH, and (i) an SR, and wherein R is one of $R_1$, and wherein $R_7$ and $R_8$ may be the same or different and is one of $R_1$;

$R_4$ is one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ is one of (a) a $NR_6R_7$, (b) a $SR_6$, (c) a $OR_6$, and (d) a $CHR_6R_7$, wherein $R_6$ and $R_7$ are one of $R_1$ and $R_2$, and $R_6$ and $R_7$ are the same when said C ring is completely or partially saturated;

X is a sulfur (S);

Y is one of (a) a nitrogen (N), (b) an oxygen (O), (c) a sulfur (S), and (d) a $CR_6$, wherein $R_6$ is one of $R_1$ and $R_3$, and wherein when Y is O or S then either $R_1$ or $R_2$ is absent;

wherein when said C ring is partially saturated and X is a sulfur (S) and Y is a sulfur (S) and $R_3$ is a hydrogen (H) or a methyl, then (a) $R_1$ is not a methyl when $R_2$ is absent; and (b) $R_2$ is not a methyl when $R_1$ is absent;

wherein when said C ring is partially saturated and X is a sulfur (S) and Y is an oxygen (O) and $R_3$ is a methyl, then (a) $R_1$ is not an ethyl or a propyl when $R_2$ is absent; and (b) $R_2$ is not an ethyl or a propyl when $R_1$ is absent;

wherein when said C ring is partially saturated and X is a sulfur (S) and Y is a nitrogen (N) and $R_3$ is a methyl, then (a) $R_1$ is not a hydrogen (H) when $R_2$ is a butyl; and (b) $R_2$ is not a hydrogen (H) when $R_1$ is a butyl; and (c) $R_1$ and $R_2$ are not both an ethyl;

wherein when X is a sulfur (S) and Y is a nitrogen (N) and $R_3$ is a hydrogen (H), then neither $R_1$ nor $R_2$ is a substituted phenyl group;

for achieving a therapeutic response.

* * * * *